US008700340B2

(12) United States Patent
Hwang et al.

(10) Patent No.: US 8,700,340 B2
(45) **Date of Patent: *Apr. 15, 2014**

(54) SEQUENCE CALIBRATION METHOD AND SEQUENCE CALIBRATION DEVICE

(75) Inventors: Bai-Kuang Hwang, Hsinchu (TW); Jenn-Yeh Fann, Hsinchu County (TW); Chao-Chi Pan, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 429 days.

This patent is subject to a terminal disclaimer.

(21) Appl. No.: 12/974,872

(22) Filed: Dec. 21, 2010

(65) Prior Publication Data

US 2011/0153249 A1 Jun. 23, 2011

Related U.S. Application Data

(60) Provisional application No. 61/282,168, filed on Dec. 23, 2009.

(51) Int. Cl.

| | |
|---|---|
| ***G06F 19/00*** | (2011.01) |
| ***C12Q 1/68*** | (2006.01) |
| ***G06F 19/22*** | (2011.01) |

(52) U.S. Cl.

CPC .............. *G06F 19/22* (2013.01); *C12Q 1/6869* (2013.01)

USPC .............................................. 702/20; 435/6.1

(58) Field of Classification Search

None

See application file for complete search history.

(56) References Cited

U.S. PATENT DOCUMENTS

2006/0024711 A1 2/2006 Lapidus et al.

FOREIGN PATENT DOCUMENTS

WO WO 2009/017678 A2 2/2009

OTHER PUBLICATIONS

Li et al. SOAP: short oligonucleotide alignment program Bioinformatics vol. 24, pp. 713-714 (2008).*

* cited by examiner

*Primary Examiner* — John S Brusca

(74) *Attorney, Agent, or Firm* — Birch, Stewart, Kolasch & Birch, LLP

(57) ABSTRACT

The invention provides a sequence calibration method, including: (a) obtaining a first reading sequence and a second reading sequence from an identical source by a receiving unit; (b) setting a comparison condition by a determining unit; and (c) comparing the first reading sequence with the second reading sequence according to the comparison condition to generate a sequence comparison result by the determining unit; and (d) outputting a calibrated sequence according to the sequence comparison result by the determining unit, wherein the comparison condition is set according to a first seed table of the first reading sequence and a second seed table of the second reading sequence.

28 Claims, 24 Drawing Sheets

```
CATACGTAGGGTGGCTAAGATACTTTTGTTCAGACACATCCCCCC  C  CTTCTCTGGCGGG    1
     * ********** ********* ****** ********** ***  *  * *** ********    *
TATGCGTAGGGTGGCTAAGATACTTTTGTTCAGATACTCCAGCCCCCCC     CCTTCGCTGGCGGG    2
 * ************* ********* ****** ******** ** ****     ***** ******    *
CATACGTAGGGTGGCTAAGATACTTTTGTTCAGACACATCCCCCC  C  TTCTCTGGCGGG          1
     * ********** ********* ****** ********** ***  *  * ** ********    *
GATACGTAGGGGGGCTACGATACTTTAGTTCAGACAACCGCCCCCGTCTTCTCTGGCGGG            3
     * ********** ********* ****** ******** *** ** **** ** *****       *
CATACGTAGGGTGGCTAAGATACTTTTGTTCAGACACATCCCCCC  C  CTTCTCTGGCGGG         1
     * ********** ********* ****** ********** ***  *  * *** *********  *
GATACGTAGGGTGGCTAAGATAC TG  T  TTCAGACACATCCCCCCGCCTTTCTCTGGCGGG        4
     * ********** ********* ****** ******** ************** **********  *
CATACGTAGGGTGGCTAAGATACTTTTGTTCAGACACATCCCCCCC T  C  TCTGGCGGG          1
     * ********** ********* ****** ********** ***  *  * * ** ******    *
GATACGTAGGGTGGCTAAGATACTGTAGTTCAGACACATCCGCACGCCTACTCTGGCTGG           5
```

FIG. 9a

```
CATACGTAGGGTGGCTAAGATACTTTGTTCAGACACATCCCCCC..CCTTCTCTGGCGGG   1
...CGTAGGGTGGCTAAGATACTTTGTTCAGA............CCTTCGCTGGCGGG    2
...ATACGTAGGGGGCTACGATACTTT GTTCAGACACA...........CTTCTCTGGCGGG   3
...ATACGTAGGGTGGCTAAGATACT  TGTTCAGACACA.........CCTTCTCTGGCGGG   4
...ATACGTAGGGTGGCTAAGATACT  GTTCAGACACATCC........CTCTGGC...    5
```

```
 ATACGTAGGGCTAAGATACTTTTGTTCAGACACA              CCTTCTCTGGCGGG
ATA         T       A        TTT          CACA               C    T
```

```
?ATACGTAGGGTGGCTAAGATACTTTTGTTCAGACACA??????CCTTCTCTGGCGGG   (Sequence
                                                              comparison result)
```

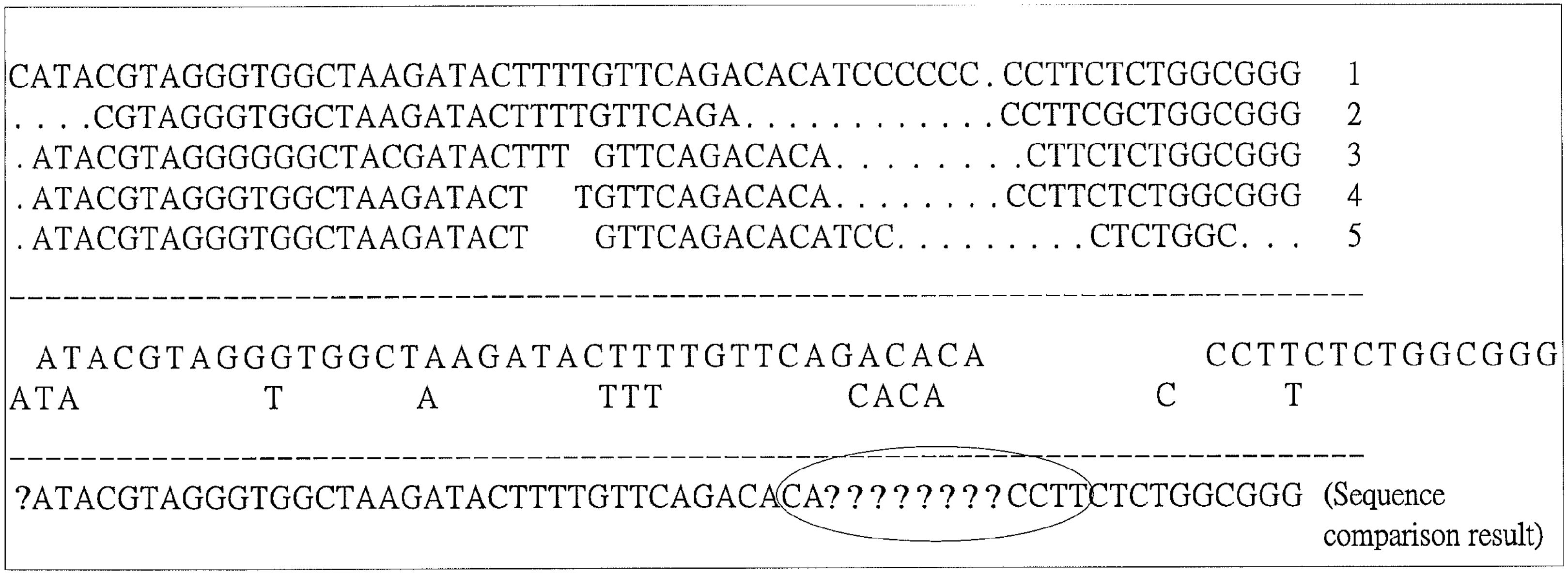

FIG. 9b

```
CATACGTAGGGTGGCTAAGATACTTTTGTTCAGACACATCCCCCC  CCTTCTCTGGCGGG   1
TATGCGTAGGGTGGCTAAGATACTTTTGTTCAGATACTCCAGCCCGCCTTCGCTGGCGGG   2
GATACGTAGGGGGGCTACGATACTTTAGTTCAGACACAACCGCCCGTCTTCTCTGGCGGG   3
GATACGTAGGGTGGCTAAGATACTG  TGTTCAGACACAACCGCCCGCCTTCTCTGGCGGG   4
GATACGTAGGGTGGCTAAGATACTGTAGTTCAGACACATCCGCACGCCTACTCTGGCTGG   5
-------------------------------------------------------------
                                                               (Sequence
?ATACGTAGGGTGGCTAAGATACTTTTGTTCAGACACA????????CCTTCTCTGGCGGG  comparison
                                                                result)
```

FIG. 9c

```
TATGCGTAGGGTGGCTAAGATACTTTTGTTCAGATACTCCAGCCCGCCTTCGCTGGCGGG  2
    ******* ***** ******** *******       ***** **** ********
GATACGTAGGGGGGCTACGATACTTTAGTTCAGACACAACCGCCCGTCTTCTCTGGCGGG  3

TATGCGTAGGGTGGCTAAGATACTTTTGTTCAGATACTCCAGCCCGCCTTCGCTGGCGGG  2
    ********************  ********       ********** ********
GATACGTAGGGTGGCTAAGATACTG TGTTCAGACACAACCGCCCGCCTTCTCTGGCGGG  4

TATGCGTAGGGTGGCTAAGATACTTTTGTTCAGATACTCCAGCCCGCCTTCGCTGGCGGG  2
    ********************   *******          *****   *****
GATACGTAGGGTGGCTAAGATACTGTAGTTCAGACACATCCGCACGCCTACTCTGGCTGG  5
```

FIG. 9d

STEP 6 : LOCAL ADJUSTMENT WITH MINIMUM PENALTY IF NECESSARY

```
?ATACGTAGGGTGGCTAAGATACTTTTGTTCAGACACA???GCCCGCCTTCTCTGGCGGG  (New sequence comparison)

CATACGTAGGGTGGCTAAGATACTTTTGTTCAGACACATCCCCCC  CCTTCTCTGGCGGG  1
TATGCGTAGGGTGGCTAAGATACTTTTGTTCAGATACTCCAGCCCGCCTTCGCTGGCGGG  2
GATACGTAGGGGGGCTACGATACTTTAGTTCAGACACAACCGCCCGTCTTCTCTGGCGGG  3
GATACGTAGGGTGGCTAAGATACTG  TGTTCAGACACAACCGCCCGCCTTCTCTGGCGGG  4
GATACGTAGGGTGGCTAAGATACTGTAGTTCAGACACATCCGCACGCCTACTCTGGCTGG  5
------------------------------------------------------------------
GTACGTAGGGTGGCTAAGATACTTTTGTTCAGACACA*CCGCCCGCCTTCTCTGGCGGG  RESULT
                      ◎                   ◎
```

FIG. 9f

```
gtacgtagggtggctaagatactttttgttcagacacatcgcccgccttctctggcggg   ORIGINAL
GTACGTAGGGTGGCTAAGATACTTTTGTTCAGACACA CCGCCCGCCTTCTCTGGCGGG   RESULT
-------------------------------------*-*---- ----------------

There are TWO miamatches.
```

FIG. 9g

TTTGAGTCTGCCCCAAAGTCTGATGACCCATTGGCTTTCCTTGTGGCCTTTTCCATAGAAGAAAATACATTACGAGTATCCTTTCAGGGAAAATCGAGGA 1
TTTGAGTCGGCCCAAAAGTCTGATGACCCAATGCCTTTCCTTGTGGCATTTTCCATTGAAGAAAGTACAGTAGGAGTATCCTCTCATGGAAAATCGAGGA 2
TTTGAGTCTGACCGAAAGTCAGATGACCCCTTGCCTGCCTTGTGGCATTTTCCATAGAAGAGAGTACAGAAAGAGTATCCATTCATGGAATATCGAGGA 3
TTGGTGTCTGCTCCAAAGTCTGATGACCCATAGCCTTTCCTTGTGGCATTTTCCATACGAGTAAGTACAGGACGAATATCCATGCGTGGAAAATCGAAGA 4
CTTGAGTCCGCCACAAAGTTTTATGACCCATTGCCTATCCTGGTGGCATTATCCATAGAAAAAAGTACAGTAGGAGTATCCGTTCATGGAAAAACGACGA 5
CTTGATTCTGCCCCAAAGTCTGATACCCCAATGCCTTTCCTTGTGGCACTATCCATAGAAGAAAGTGCAGTAGGGGTATCCAGGTAAGGAAAATCGAGGA 6
TTTGAGTCTGCCTCAAAGTCTTATAACCCATTGCCTTTTCTTGTGGCATCTTCCCTAGAAAAGGTCCAGTACGAGTATCCATTCATGGATAACCGAGGA 7
TTTGAGACTGCCCCAAAGTCTGATTATCCATTGTCTGTCCTTGGGGCATTTTACATAGAAGAAAGTACAGTAGGAGTATACAATCCTGGAAAATCGAGGA 8
TTTGAGTCTGCCCCACAGACTGATGACCAATTGCCTTTCGTTGTGGTATTTTCGAAAGAAGAAAGTACGATAGGAGTATTCATTCATGGTTAATCGAGGA 9

FIG. 10a

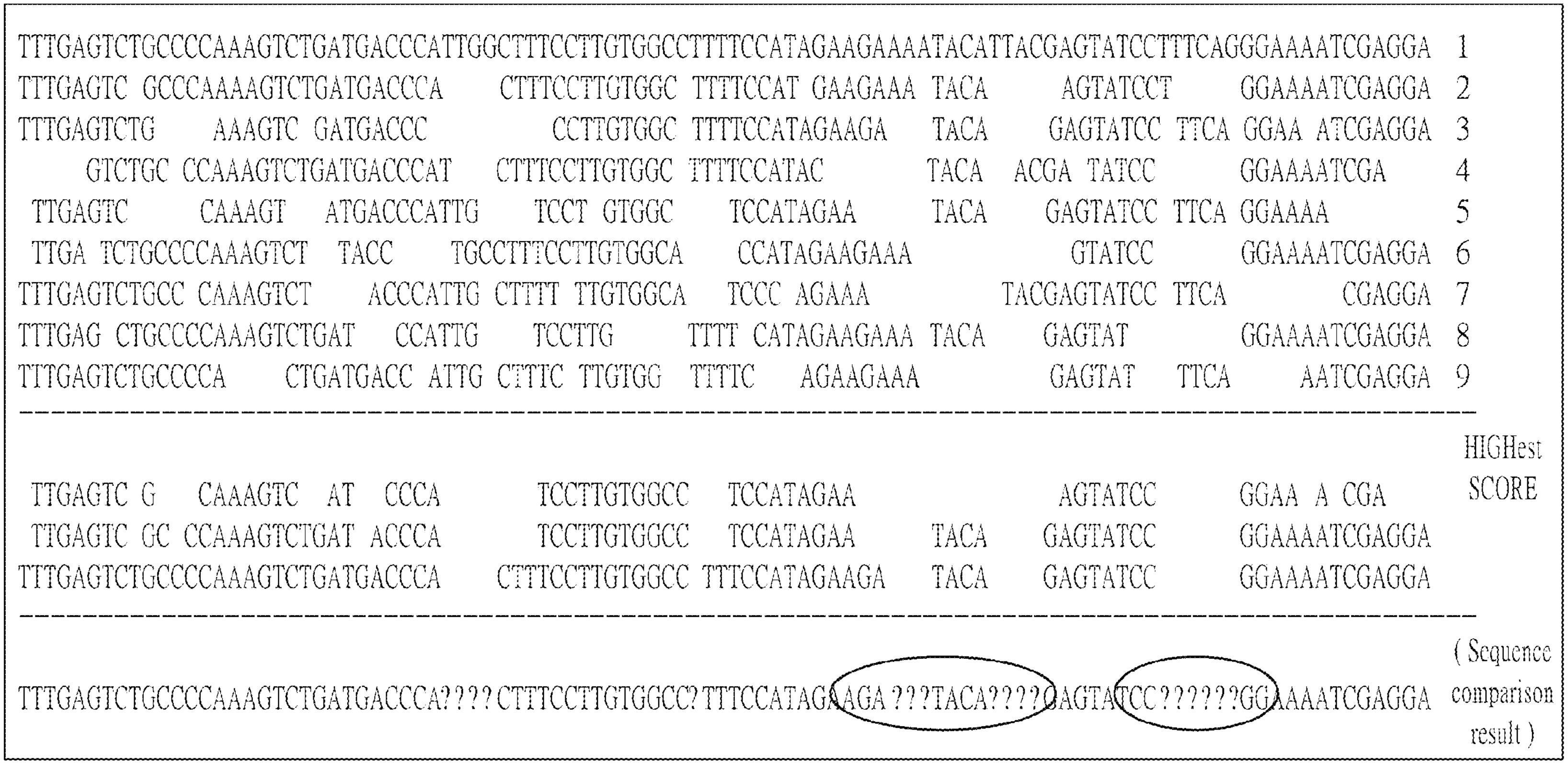

FIG. 10c

| | | | | |
|---|---|---|---|---|
| TTTGAGTCTGCCCAAAGTCTGATGACCCATTGGCTTTCCTTGTGGCCTTTTCATAGAGAAAATACATTACGAGTATCCTTTCAGGGAAAAATCGAGGA | | | | 1 |
| TTTGAGTC GCCCAAAGTCTGATGACCCA | CTTTCCTTGTGGC | TTTTCCAT GAAGAAA TACA | AGTATCCT | GGAAAATCGAGGA | 2 |
| TTTGAGTCTG AAAGTC GATGACCC | CCTTGTGGC | TTTTCCATAGAAGA TACA | GAGTATCC TTCA | GGAA ATCGAGGA | 3 |
| GTCTGC CCAAAGTCTGATGACCCAT | CTTTCCTTGTGGCC | TTTTCCATAC TACA | ACGA TATCC | GGAAAATCGA | 4 |
| TTGAGTC CAAAGT ATGACCCATTG | TCCT GTGGC | TCCATAGAA TACA | GAGTATCC TTCA | GGAAAA | 5 |
| TTGA TCTGCCCCAAAGTCT TACC | TGCCTTTCCTGTGGCA | CCATAGAAGAAA | GTATCC | GGAAAATCGAGGA | 6 |
| TTTGAGTCTGCC CAAAGTCT ACCCATTG CCATTG | CTTTT TTGTGGCA | TCCC AGAA | TACCGAGTATCC TTCA | CCGAGGA | 7 |
| TTTGAG CTGCCCAAAGTCTGAT CCATTG | TCCTTG | TTTT CATAGAAGAAA TACA | GAGTAT | GGAAAATCGAGGA | 8 |
| TTTGAGTCTGCCCCA CTGATGACC | ATTG CTTTC TTGTGG | TTTTC AGAAGAA | GAGTAT TTCA | AATCGAGGA | 9 |

HIGHest SCORE

```
TTTGAGTCTGCCCCAAAGTCTGATGACCCATTGGCTTTCCTTGTGGCCTTTTCCATAGAAGAAAATACATTACGAGTATCCTTTCAGGGAAAATCGAGGA  1
TTTGAGTCGGCCCAAAAGTCTGATGACCCAATGCCTTTCCTTGTGGCATTTTCCATTGAAGAAAGTACAGTAGGAGTATCCTCTCATGGAAAATCGAGGA  2
TTTGAGTCTGACCGAAAGTCAGATGACCCCTTGCCTG CTTTGTGGCATTTTCCATAGAAGAGAGTACAGAAAGAGTATCCATTCATGGAATATCGAGGA  3
TTGGTGTCTGCTCCAAAGTCTGATGACCCATAGCCTTTCCTTGTGGCATTTTCCATACGAGTAAGTACAGGACGAATATCCATGCGTGGAAAATCGAAGA  4
CTTGAGTCCGCCACAAAGTTTTATGACCCATTGCCTATCCTGGTGGCATTATCCATAGAAAAAAGTACAGTAGGAGTATCCGTTCATGGAAAAACGACGA  5
CTTGATTCTGCCCCAAAGTCTGATACCCCAATGCCTTTCCTTGTGGCACTATCCATAGAAGAAAGTGCAGTAGGGGTATCCAGGTAAGGAAAATCGAGGA  6
TTTGAGTCTGCCTCAAAGTCTTATAACCCATTGCCTTTTCTTGTGGCATCTTCCCTAGAAAAGGTCCAG TACGAGTATCCATTCATGGATAACCGAGGA  7
TTTGAGACTGCCCCAAAGTCTGATTATCCATTGTCTGTCCTTGGGGCATTTTACATAGAAGAAAGTACAGTAGGAGTATACAATCCTGGAAAATCGAGGA  8
TTTGAGTCTGCCCCACAGACTGATGACCAATTGCCTTTCGTTGTGGTATTTTCGAAAGAAGAAAGTACGATAGGAGTATTCATTCATGGTTAATCGAGGA  9
-----------------------------------------------------------------------------------------------------
TTTGAGTCTGCCCCAAAGTCTGATGACCCA????CTTTCCTTGTGGCC?TTTCCATAGAAGA???TACA????GAGTATCC??????GGAAAATCGAGGA  (Sequence comparison result)
```

FIG. 10d

TTTGAGTCTGCCCCAAAGTCTGATGACCCA????CTTTCCTTGTGGCC?TTTCCATAGAAGA???TACA????GAGTATCC?????GGAAAATCGAGGA (Comparison Resulting Sequence)

TTTGAGTCTGCCCCAAAGTCTGATGACCCATTGGCTTTCCTTGTGGCCTTTTCCATAGAAGAAAATACATTAGGAGTATCCTTTCAGGGAAAATCGAGGA 1
TTTGAGTCGGCCAAAGTCTGATGACCCATTTCCTTGTGGCATTTTCCATTGAAGAAAGTACAGTAGGAGTATCCTCTCATGGAAAATCGAGGA 2
TTTGAGTCTGACCGAAAGTCAGATGACCCCTTGCCTG(CCTTG)TGGCATTTTCCATAGAAGAGAGTACAGAAGAGTATCCATTCATGGAATATCGAGGA 3
TTGGTGTCTGCTCCAAAGTCTGATGACCCATAGCCTTTCCTGTGGCATTTTCCATACGAGTAGTAGTACAGGAGTAATCCATGCGTGGAAAATCGAAGA 4
CTTGAGTCCCGCCAAAGTTTATGACCCAATGCCTATCCTGTGGCATTATCCATAGAAAAAAGTACAGTAGGAGTATCCGTTCATGGAAAACGACGA 5
CTTGATTCGCCCCAAAGTCTGATACCCCAATGCCTTTCCTTCCTGTGGCACTATCCATAGAAGAAGAAAGTGCAGTAGGGGTATCCAGGTAAGAAAATCGAGGA 6
TTTGAGTCTGCCTCAAAGTCTTATAACCCATTGCCTTTTCTGTGGCATCTCCCTAGAAAAGGTCCAG TAC(GAGTA)TCCATTCATGATAACCGAGGA 7
TTTGAGACTGCCCAAAGTCTGATTATCCATTGCTGTCGTCCTTGGGCATTTACATAGAAGAAAGTACAGTAGAA GTATACAACTCTGAAAATCGAGGA 8
TTTGAGTCTGCCCACAGACTGATGACCCATTGCCTTTCGTTGTGGTATTTCGAAAAGAAGAAGTACGATAGGAGTATTCATTCATGTTAATCGAGGA 9

---

TTTGAGTCTGCCCCAAAGTCTGATGACCCATTGGCTTTCCTTGTGGCCTTTTCCATAGAAGAAAATACATTAGGAGTATCCTTTCAGGGAAAATCGAGGA (Result)

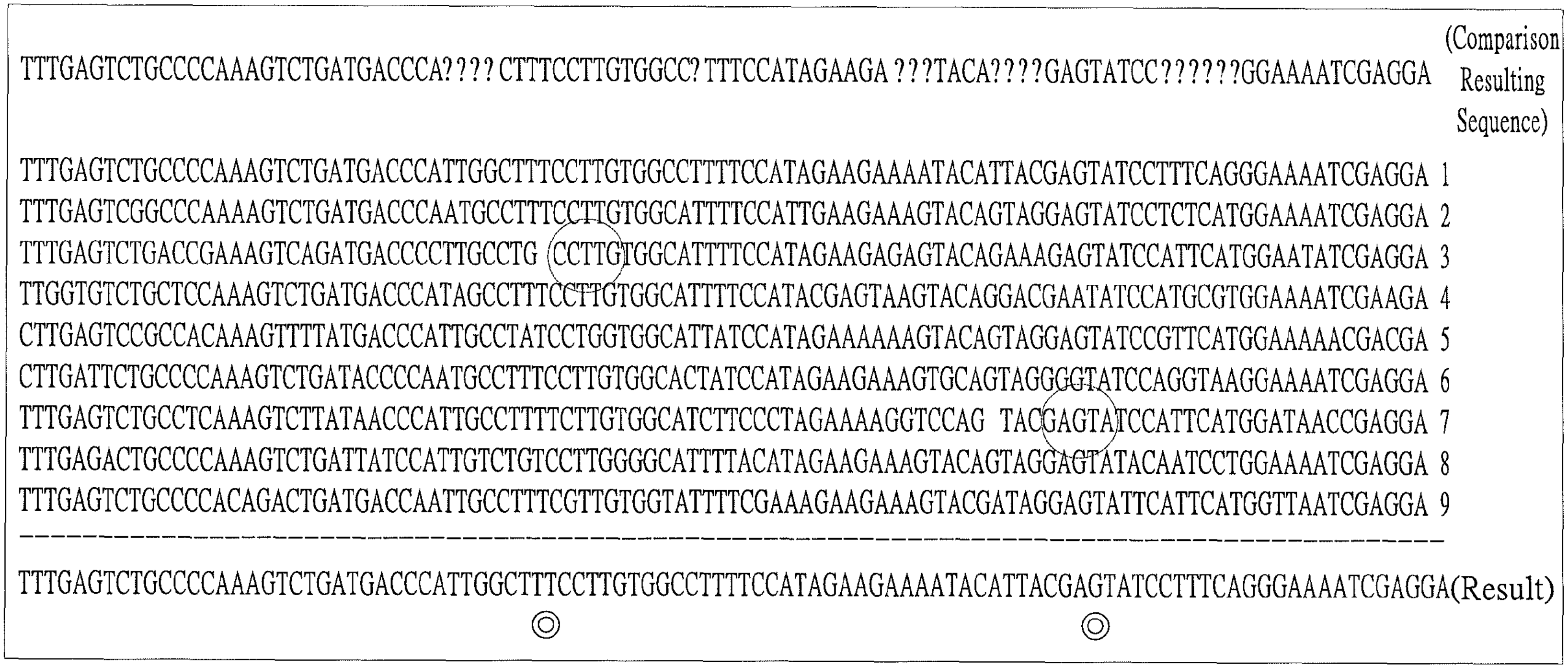

FIG. 10e

TTTGAGTCTGCCCCAAAGTCTGATGACCCATTGGCTTTCCTTGTGGCCTTTTCCATAGAAGAAAATACATTACGAGTATCCTTTCAGGGAAAATCGAGGA (Original)
TTTGAGTCTGCCCCAAAGTCTGATGACCCATTGGCTTTCCTTGTGGCCTTTTCCATAGAAGAAAATACATTACGAGTATCCTTTCAGGGAAAATCGAGGA Result There is NO miamatch.

FIG. 10f

SEQUENCE CALIBRATION METHOD AND SEQUENCE CALIBRATION DEVICE

CROSS REFERENCE TO RELATED APPLICATIONS

This application claims the benefit of U.S. Provisional Application No. 61/282,168, filed on Dec. 23, 2009, the entirety of which is incorporated by reference herein.

INCORPORATION BY REFERENCE OF SEQUENCE LISTING

A sequence listing submitted as a text file via EFS-Web is incorporated herein by reference. The text file containing the sequence listing is named "9044-A23432-US_Seq_Listing.txt"; its date of creation is Dec. 13, 2010; and its size is 1,662 bytes.

BACKGROUND OF THE INVENTION

1. Field of the Invention

The present invention relates to a sequence calibration method, and in particular relates to a seed based sequence calibration method.

2. Description of the Related Art

A. The Development of Single-Molecule Sequencing Technology

Recently, there have been many developmental breakthroughs in methods for genomic sequencing. Traditional sequencing methods use a group of amplified DNA molecules as a replicating template (Nucleic Acids Research 2000, v28, No. 20e87; Nature 2005, v437, 376-380). Sequencing a group of template molecules means to synthesize approximately more than one thousand copies of a DNA template in one reaction at the same time. As the multi-molecule enzymatic reaction can not be 100 percent synchronized, various errors may occur in each individual molecule of a bulk nucleic acid polymerization reaction. Accordingly, interpretation of signals become more and more difficult, as more and more mixed signals are produced due to errors caused by the increasing number of nucleotides joining in a strand. Therefore, by using the traditional sequencing methods, the processing length and accuracy for sequencing are limited. Also, the traditional sequencing methods are complex, which makes subsequent sequence assembly more difficult.

Accordingly, methods for single molecule sequencing use one nucleic acid molecule as a template for a sequencing reaction (Proc. Natl. Acad. Sci., 100: 3960-64, 2003). Thus, the problem associated with interpretation of signals becoming more and more difficult, as more and more mixed signals are produced due to errors caused by the increasing number of nucleotides joining in a strand, may be mitigated. Also, the length of recognizable sequences may be increased.

B. Using Repeated Sequencing Method and the Sequences Calibration Method to Improve the Accuracy of Single Molecule DNA Sequencing Despite advantages of single molecule sequencing, for raw data, error rates are much higher than that of traditional sequencing methods. Basically, because the signal of a single fluorescent molecule is very weak, random errors produced from a single molecular sequencing reaction are directly presented in raw data. Note that unlike multi-molecular sequencing, for single molecule sequencing, ensemble averaging may not be used. Thus, a low cost, fast and accurate single molecular sequencing is required. For example, for a circular DNA molecule, if sequencing reactions, by rolling-circle amplification, may be repeatedly performed, the probability for random errors may decrease. Basically, repeated readings of a same DNA segment may be calibrated by comparison there among, for error correction. (US2006/0024711 A1, WO2009/017678 A2)

C. Analysis of the Prior Art

The traditional methods for sequence comparison, such as the Smith-Waterman, Needleman-Wunsch, FASTA, BLAST and FLAG methods, deploy "dynamic programming" algorithm and its derivations as kernels. These methods show a computing complexity higher than $O(N^2)$ when multiple sequences need to be repeatedly compared. However, these methods, which are based on sequence diversity due to biological evolution, may result in bias, if they are used to compare sequences resulting from multiple reads of one replication template.

Comparative analysis of traditional algorithms for sequence comparison

| | Needle-Wunsch.[a] | FASTA[b] | Smith-Waterman[c] | BLAST2[d] | FLAG[e] |
|---|---|---|---|---|---|
| Features | Global | Global | Local | Local | Local |
| Complexity | $>O(N^2)$ | $>O(N^2)$ | $>O(N^2)$ | $>O(N^2)$ | O(N * logN) |
| Speed | Slow | Slow | Slow | Fast | Fast |
| Resource | High | High | High | High | Medium |

The Needleman-Wunsch algorithm
FASTA software
The Smith-Waterman algorithm
The BLAST algorithm
FLAG algorithm D. Comparison of Method/Algorithm for Calibrating Sequences with Repeated Formats with Other Related Inventions In order to overcome the difficulties of traditional methods, which include complexity, slow speed and comparative bias, this invention disclosures a seed-based, multi-layer calibration method.

A seed-based, multi-layer calibration algorithm kernel is used. First, sequence seed sets of various lengths are constructed on multiple process layers. Then, sequences are progressively and downwardly calibrated from the set of the longest seeds. Thus, because neither extensions nor best path calculations are needed, the novel method reduces computing complexity and achieves high speeds.

The method of this invention can be applied to a fluorescence detection module output device of a nucleic acid single molecule sequencer based on rolling-cycle replication. The resulting sequence read consists of repeated primer parts, with a known sequence, and target DNA parts. Both parts can be identified by comparing the raw data read to the known primer sequence. Following, the identified parts are subjected to sequence extraction in repeated format. Thereafter, the extracted parts are applied in a sequence calibration process, which includes building seed tables (seed sets) and then comparing sequences thereof. Because the possibility of reading a "wrong" same base at a same position is much lower than reading a "right" same base at a same position, common sequences between two repeated may represent a more likely possibility that the sequence may be the original sequence of the template sequence.

In contrast to a large number of sequence comparisons being required to be performed for traditional methods, the novel method of this invention employs minimal process steps. Additionally, the novel method of this invention uses only seed-set comparisons to achieve high speeds.

BRIEF SUMMARY OF THE INVENTION

The invention provides a sequence calibration method, comprising: (a) obtaining a first reading sequence and a second reading sequence from an identical source by a receiving unit; (b) setting a comparison condition by a determining unit; and (c) comparing the first reading sequence with the second reading sequence according to the comparison condition to generate a sequence comparison result by the determining unit; and (d) outputting a calibrated sequence according to the sequence comparison result by the determining unit, wherein the comparison condition is set according to a first seed table of the first reading sequence and a second seed table of the second reading sequence, wherein the first seed table of the first reading sequence comprises a plurality of first seeds with a specific length constituting a plurality of first seed sets with different seeding start sites and the second seed table of the second reading sequence comprises a plurality of second seeds with a specific length constituting a plurality of second seed sets with different seeding start sites, and wherein the specific length of the first seeds of the first seed table and the specific length of the second seeds of the second seed table are of the same specific length.

The invention also provides a sequence calibration method, comprising: (a) obtaining a plurality of reading sequences from an identical source by a receiving unit; (b) selecting one of the plurality of reading sequences as a template sequence by the determining unit; (c) setting a comparing condition by a determining unit; (d) comparing the template sequence to each of the other sequences according to the comparison condition, to respectively generate comparison results by the determining unit; (e) generating a sequence comparison result according to all respectively generated comparison results by the determining unit; and (f) outputting a calibrated sequence according to the sequence comparison result by the determining unit, wherein the comparison condition is set according to a first seed table of the template sequence and second seed tables for reading sequences which are not selected, wherein the first seed table of the template sequence comprises a plurality of first seeds with a specific length constituting a plurality of first seed sets with different seeding start sites and the second seed table of the reading sequence which is not selected comprises a plurality of second seeds with a specific length constituting a plurality of second seed sets with different seeding start sites, and wherein the specific length of the first seeds of the first seed table and the specific length of the second seeds of the second seed table are of the same specific length.

The invention further provides a sequence calibration device, comprising: a receiving unit for obtaining a first reading sequence and a second reading sequence from an identical source; and a determining unit for performing steps which comprise: (a) setting a comparison condition; (b) comparing the first reading sequence with the second reading sequence according to the comparison condition to generate a sequence comparison result; and (c) outputting a calibrated sequence according to the sequence comparison result, wherein the comparison condition is set according to a first seed table of the first reading sequence and a second seed table of the second reading sequence, wherein the first seed table of the first reading sequence comprises a plurality of first seeds with a specific length constituting a plurality of first seed sets with different seeding start sites and the second seed table of the second reading sequence comprises a plurality of second seeds with a specific length constituting a plurality of second seed sets with different seeding start sites, and wherein the specific length of the first seeds of the first seed table and the specific length of the second seeds of the second seed table are of the same specific length.

The invention further provides a a sequence calibration device, comprising: a receiving unit for obtaining a plurality of reading sequences from an identical source; and a determining unit for performing steps which comprise: (a) selecting one of the plurality of reading sequences as a template sequence; (b) setting a comparison condition; (c) comparing the template sequence to each of the other sequences according to the comparison condition, to respectively generate comparison results; (d) generating a sequence comparison result according to all respectively generated comparison results; and (e) outputting a calibrated sequence according to the sequence comparison result, wherein the comparison condition is set according to a first seed table of the template sequence and second seed tables for reading sequences which are not selected, wherein the first seed table of the template sequence comprises a plurality of first seeds with a specific length constituting a plurality of first seed sets with different seeding start sites and the second seed table of the reading sequence which is not selected comprises a plurality of second seeds with a specific length constituting a plurality of second seed sets with different seeding start sites, and wherein the specific length of the first seeds of the first seed table and the specific length of the second seeds of the second seed table are of the same specific length.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein:

FIGS. 9*a*-9*g* show procedures of the sequence calibration method of Example 1. In FIG. 9*a*, the sequence numbered as 1 is the sequence of SEQ ID NO. 2, the sequence numbered as 2 is the sequence of SEQ ID NO. 3, the sequence numbered as 3 is the sequence of SEQ ID NO. 4, the sequence numbered as 4 is the sequence of SEQ ID NO. 5, and the sequence numbered as 5 is the sequence of SEQ ID NO. 6. In FIG. 9*b*, the sequence numbered as 1 is the sequence of SEQ ID NO. 2, the sequence numbered as 2 is the sequence of SEQ ID NO. 3, which only shows the nucleotides the same as the nucleotides at the corresponding site of SEQ ID NO. 2, the sequence numbered as 3 is the sequence of SEQ ID NO. 4, which only shows the nucleotides the same as the nucleotides at the corresponding site of SEQ ID NO. 2, the sequence numbered as 4 is the sequence of SEQ ID NO. 5, which only shows the nucleotides the same as the nucleotides at the corresponding site of SEQ ID NO. 2, and the sequence numbered as 5 is the sequence of SEQ ID NO. 6, which only shows the nucleotides the same as the nucleotides at the corresponding site of SEQ ID NO. 2, and the sequence indicated by the term "Sequence comparison result" is the sequence of SEQ ID NO. 7. In FIG. 9*c*, the sequence numbered as 1 is the sequence of SEQ ID NO. 2, the sequence numbered as 2 is the sequence of SEQ ID NO. 3, the sequence numbered as 3 is the sequence of SEQ ID NO. 4, the sequence numbered as 4 is the sequence of SEQ ID NO. 5, and the sequence numbered as 5 is the sequence of SEQ ID NO. 6, and the sequence indicated by the term "Sequence comparison result" is the sequence of SEQ ID NO. 7. In FIG. 9*d*, the sequence numbered as 2 is the sequence of SEQ ID NO. 3, the sequence numbered as 3 is the sequence of SEQ ID NO. 4, the sequence numbered as 4 is the sequence of SEQ ID NO. 5, and the sequence numbered as 5 is the sequence of SEQ ID NO. 6. In FIG. 9*e*., the sequence indicated by the term "Sequence comparison result" is the sequence of SEQ ID NO. 7, the sequence numbered as 3 is the sequence of SEQ ID NO. 4, which only shows the nucleotides at the positions 5-11, 13-17, 19-26, 28-32, 42-51 and 52-60, the sequence numbered as 4 is the sequence of SEQ ID NO. 5, which only shows the nucleotides at the positions 5-24, 26-31, 41-50 and 52-59, the sequence numbered as 5 is the sequence of SEQ ID NO. 6, which only shows the nucleotides at the positions 5-24, 28-32, 45-49 and 53-57, and the sequence indicated by the term "New sequence comparison" is the sequence of SEQ ID NO. 7. In FIG. 9*f*, the sequence indicated by the term "New sequence comparison" is the sequence of SEQ ID NO. 8, the sequence numbered as 1 is the sequence of SEQ ID NO. 2, the sequence numbered as 2 is the sequence of SEQ ID NO. 3, the sequence numbered as 3 is the sequence of SEQ ID NO. 4, the sequence numbered as 4 is the sequence of SEQ ID NO. 5, and the sequence numbered as 5 is the sequence of SEQ ID NO. 6, and the sequence indicated by the term "RESULT" is the sequence of SEQ ID NO. 9. In FIG. 9*g*, the sequence indicated by the term "ORIGINAL" is the sequence of SEQ ID NO. 1, and the sequence indicated by the term "RESULT" is the sequence of SEQ ID NO. 9.

FIGS. 10*a*-10*f* show procedures of the sequence calibration method of Example 2. In FIG. 10*a*, the sequence numbered as 1 is the sequence of SEQ ID NO. 11, the sequence numbered as 2 is the sequence of SEQ ID NO. 12, the sequence numbered as 3 is the sequence of SEQ ID NO. 13, the sequence numbered as 4 is the sequence of SEQ ID NO. 14, the sequence numbered as 5 is the sequence of SEQ ID NO. 15, the sequence numbered as 6 is the sequence of SEQ ID NO. 16, the sequence numbered as 7 is the sequence of SEQ ID NO. 17, the sequence numbered as 8 is the sequence of SEQ ID NO. 18, and the sequence numbered as 9 is the sequence of SEQ ID NO. 19. In FIG. 10*b*, the sequence numbered as 1 is the sequence of SEQ ID NO. 11, the sequence numbered as 2 is the sequence of SEQ ID NO. 12, the sequence numbered as 3 is the sequence of SEQ ID NO. 13, the sequence numbered as 4 is the sequence of SEQ ID NO. 14, the sequence numbered as 5 is the sequence of SEQ ID NO. 15, the sequence numbered as 6 is the sequence of SEQ ID NO. 16, the sequence numbered as 7 is the sequence of SEQ ID NO. 17, the sequence numbered as 8 is the sequence of SEQ ID NO. 18, and the sequence numbered as 9 is the sequence of SEQ ID NO. 19. In FIG. 10*c*, the sequence numbered as 1 is the sequence of SEQ ID NO. 11, the sequence numbered as 2 is the sequence of SEQ ID NO. 12, which only shows the nucleotides the same as the nucleotides at the corresponding site of SEQ ID NO. 11, the sequence numbered as 3 is the sequence of SEQ ID NO. 13, which only shows the nucleotides the same as the nucleotides at the corresponding site of SEQ ID NO. 11, the sequence numbered as 4 is the sequence of SEQ ID NO. 14, which only shows the nucleotides the same as the nucleotides at the corresponding site of SEQ ID NO. 11, the sequence numbered as 5 is the sequence of SEQ ID NO. 15, which only shows the nucleotides the same as the nucleotides at the corresponding site of SEQ ID NO. 11, the sequence numbered as 6 is the sequence of SEQ ID NO. 16, which only shows the nucleotides the same as the nucleotides at the corresponding site of SEQ ID NO. 11, the sequence numbered as 7 is the sequence of SEQ ID NO. 17, which only shows the nucleotides the same as the nucleotides at the corresponding site of SEQ ID NO. 11, the sequence numbered as 8 is the sequence of SEQ ID NO. 18, which only shows the nucleotides the same as the nucleotides at the corresponding site of SEQ ID NO. 11, and the sequence numbered as 9 is the sequence of SEQ ID NO. 19, which only shows the nucleotides the same as the nucleotides at the corresponding site of SEQ ID NO. 11, and the sequence indicated the term "Sequence comparison result" is the sequence of SEQ ID NO. 20. In FIG. 10*d*, the sequence numbered as 1 is the sequence of SEQ ID NO. 11, the sequence numbered as 2 is the sequence of SEQ ID NO. 12, the sequence numbered as 3 is the sequence of SEQ ID NO. 13, the sequence numbered as 4 is the sequence of SEQ ID NO. 14, the sequence numbered as 5 is the sequence of SEQ ID NO. 15, the sequence numbered as 6 is the sequence of SEQ ID NO. 16, the sequence numbered as 7 is the sequence of SEQ ID NO. 17, the sequence numbered as 8 is the sequence of SEQ ID NO. 18, and the sequence numbered as 9 is the sequence of SEQ ID NO. 19, and the sequence indicated by the term "Sequence comparison result" is the sequence of SEQ ID NO. 20. In FIG. 10*e*, the sequence indicated by the term "Comparison Resulting Sequence" is the sequence of SEQ ID NO. 20, the sequence numbered as 1 is the sequence of SEQ ID NO. 11, the sequence numbered as 2 is the sequence of SEQ ID NO. 12, the sequence numbered as 3 is the sequence of SEQ ID NO. 13, the sequence numbered as 4 is the sequence of SEQ ID NO. 14, the sequence numbered as 5 is the sequence of SEQ ID NO. 15, the sequence numbered as 6 is the sequence of SEQ ID NO. 16, the sequence numbered as 7 is the sequence of SEQ ID NO. 17, the sequence numbered as 8 is the sequence of SEQ ID NO. 18, and the sequence numbered as 9 is the sequence of SEQ ID NO. 19, and the sequence indicated by the term "Result" is the sequence of SEQ ID NO. 21. In FIG. 10*f*, the sequence indicated by the term "original" is the sequence of SEQ ID NO. 10, and the sequence indicated by the term "Result" is the sequence of SEQ ID NO. 21.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides a sequence calibration method and a device for performing the sequence calibration method.

In the invention, the foundation of the sequence calibration method is to compare two sequences.

The sequence calibration method is detailed in the following, in one aspect of the invention.

Figure 1:
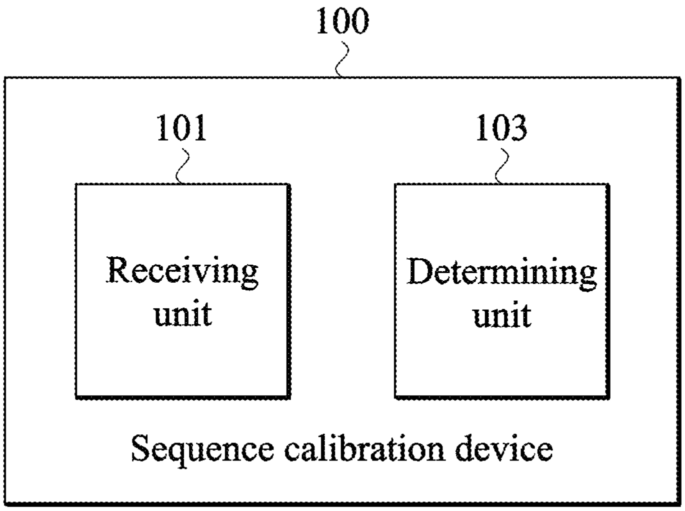
FIG. 1 shows a diagram of one embodiment of a sequence calibration device of the invention.
Figure 2A:
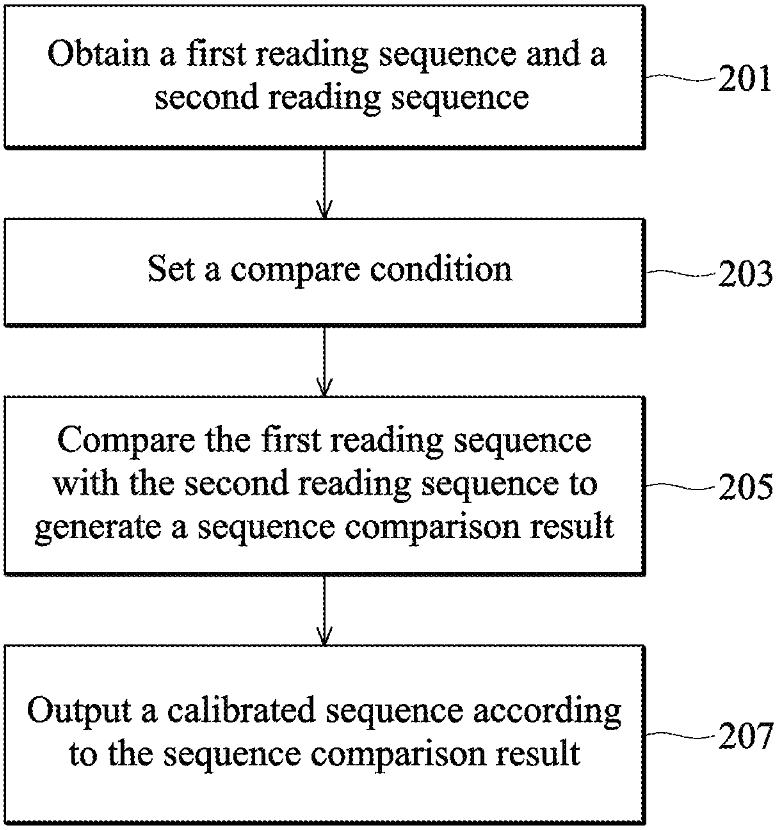
FIG. 2*a* shows a simplified flow chart of one embodiment of a sequence calibration method for two reading sequences.

Referring to FIG. 1 and FIG. 2*a*, FIG. 1 shows a diagram of one embodiment of a sequence calibration device of the invention and FIG. 2*a* shows a simplified flow chart of one embodiment of the sequence calibration method performed by the device. The sequence calibration device 100 may comprises a receiving unit 101 and a determining unit 103. First, the receiving unit 101 obtains a first reading sequence and a second reading sequence from an identical source (step 201). Next, the determining unit 103 sets a comparison condition (step 203). After the comparison condition is set, the determining unit 103 compares the first reading sequence with the second reading sequence according to the comparison condition to generate a sequence comparison result (step 205). Then, the determining unit 103 outputs a calibrated sequence according to the sequence comparison result (step 207).

The determining unit 103 may set the comparison condition according to a first seed table of the first reading sequence and a second seed table of the second reading sequence. The first seed table of the first reading sequence may comprise a plurality of first seeds with a specific length constituting a plurality of first seed sets with different seeding start sites and the second seed table of the second reading sequence may comprise a plurality of second seeds with a specific length constituting a plurality of second seed sets with different seeding start sites, wherein the specific length of the first seeds of the first seed table and the specific length of the second seeds of the second seed table are of the same specific length.

A seed table of a sequence may be built by the determining unit 103, wherein a seed is a segment of the sequence. An example of building a seed table of a sequence is detailed in the following.

A sequence is divided into a plurality of seeds (or segment) sets from the different start sites of the sequence, respectively, by per seed (or segment) K mers (a specific length of the seeds), wherein K is a positive integer of greater than 2, preferably 2-9, more preferably 3-9 and a content and a position of each seed are recorded, and then a seed table of the sequence is built. The basis for choosing the specific length of the seeds for dividing the sequence may comprise experiences of a user, the length of the sequence or the accuracy of a prior calibrated sequence from the calibration method of the invention, but not limited thereto, wherein the accuracy of a prior calibrated sequence may be obtained by comparing a know sequence of a know primer with the calibrated sequence thereof obtained from the calibration method of the invention. In one embodiment, the specific length per seed may be chosen according to experiences of a user. In another embodiment, the specific length per seed is chosen according to the length of the sequence. In further another embodiment, the specific length per seed is chosen according to a prior calibrated sequence.

For example, when K is 4, a seed table of a sequence is built as follows.

The sequence is divided into a plurality of seeds from the first base by per seed 4 mers, wherein the plurality of seeds therefrom is called a shift-0 seed set, and a content and a position of each seed are recorded.

Next, the sequence is divided into a plurality of seeds from the second base by per seed 4 mers, wherein the plurality of seeds therefrom is called a shift-1 seed set, and a content and a position of each seed are recorded.

Then, the sequence is divided into a plurality of seeds from the third base by per seed 4 mers, wherein the plurality of seeds therefrom is called a shift-2 seed set, and a content and a position of each seed are recorded.

After that, the sequence is divided into a plurality of seeds from the forth base by per seed 4 mers, wherein the plurality of seeds therefrom is called a shift-3 seed set, and a content and a position of each seed are recorded.

Finally, according to each seed set and the seeds therein mentioned above, a seed table with 4 mer length (4-mer seed table) is built. Note that a seed table with other seed length of the sequence may be built with a similar approach.

In addition, it is noted that the seed tables with different seed lengths (from the longest seed length need to the shortest seed length (2 mers)) of a sequence may be built at the same time. Or only a seed table with a specific length of a sequence may be built and the rest of the seed tables with other seed lengths may be built when needed.

The conditional ordering schedule for comparing the specific seed length tables of the reading sequences in the invention is to first compare the longest seed length tables of the reading sequences, and continue comparisons to the shortest seed length tables of the reading sequences.

Figure 2B:
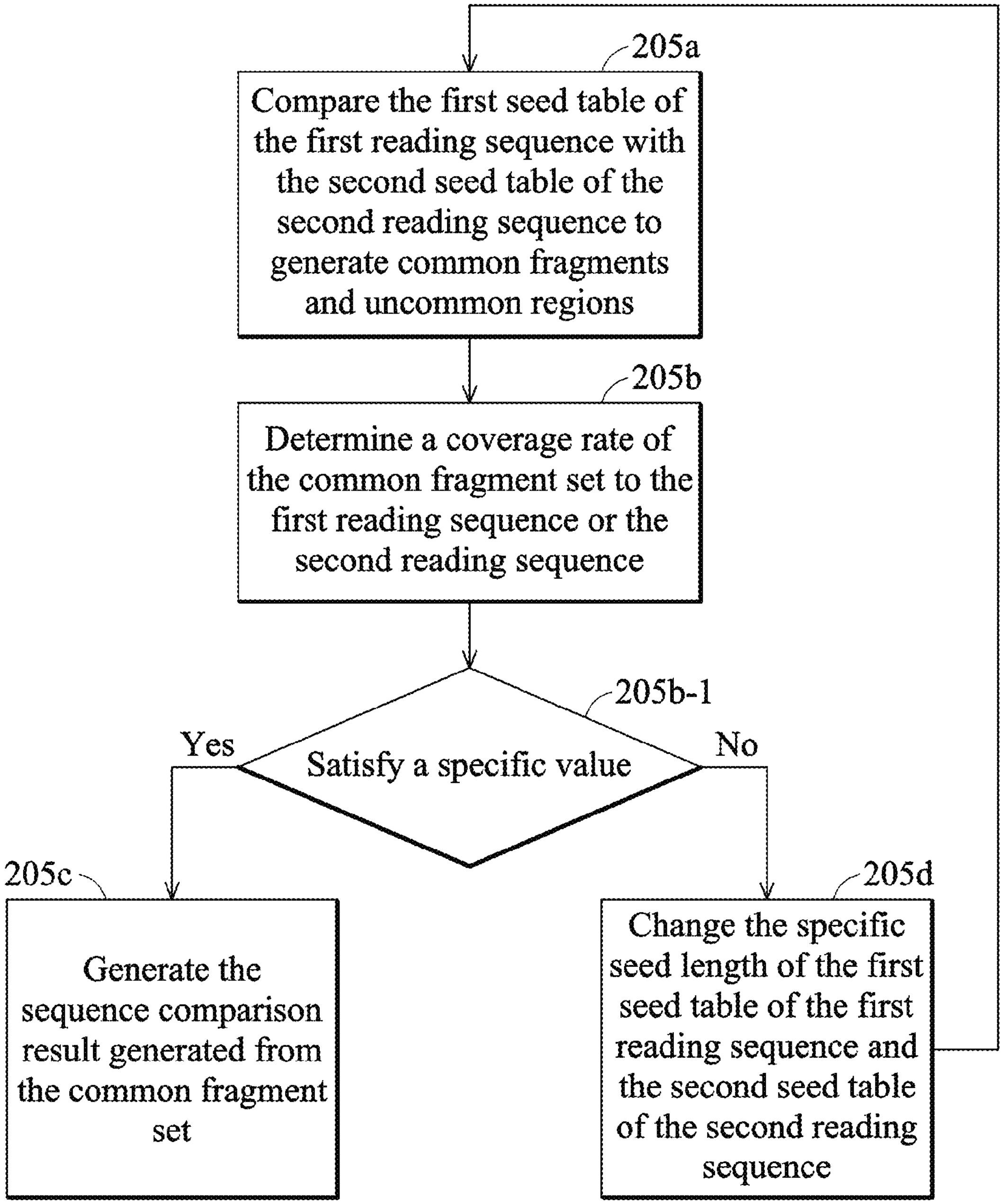
FIG. 2*b* shows a simplified flow chart of one embodiment of step 205 of FIG. 2*a;*

In one embodiment, see FIG. 2*b*, when the determining unit 103 compares the first reading sequence with the second reading sequence according to the comparison condition to generate a sequence comparison result (step 205), the determining unit 103 may compare the first seed table of the first reading sequence with the second seed table of the second reading sequence to generate common fragments and uncommon regions (step 205*a*). One common fragment consists of at least one common seed and is between two uncommon regions without interruption, and the longer the common fragment is, the greater the amount of the common seed contained therein is. All common fragments generated by comparing the first seed table with the second seed table form a common fragment set. The common seed is defined as the seed of the first reading sequence and the seed of the second reading sequence, when the content of a seed of the first reading sequence and a seed of the second reading sequence at a corresponding region or a region close to the corresponding region are equivalent. After comparing the first seed table of the first reading sequence with the second seed table of the second reading sequence to generate common fragments and uncommon regions (step 205*a*), the determining unit 103 then determines a coverage rate of the common fragment set to the first reading sequence or the second reading sequence (step 205 *b*). After that, when the value of the coverage rate satisfies a predetermined value, the determining unit 103 generates the sequence comparison result from the common fragment set (step 205 *c*). The value of the predetermined value is not limited, and may be 80-95%, or preferably 95%.

Comparatively, when the value of the coverage rate does not satisfy a predetermined value, the determining unit 103 changes the specific length of the first seeds constituting the first seed table of the first reading sequence and the specific length of the second seeds constituting the second seed table of the second reading sequence (i.e. changing the seed table of the first reading sequence with the specific seed length used in the comparison to the other seed table of the first reading sequence with the other specific seed and changing the seed table of the second reading sequence with the specific seed length used in the comparison to the other seed table of the second reading sequence with the other specific seed)) (step 205*d*). Next, the determining unit 103 compares the first seed table constituted by the first seeds with the changed specific length with the second seed table constituted by the second seeds with the changed specific length at the uncommon regions (step 205*a*) to generate second common fragments and second uncommon regions, wherein the second common fragments and the first common fragment set constitute a second common fragment set, determines a coverage rate of the second common fragment set to the first reading sequence or the second reading sequence (step 205*b*) and generates the sequence comparison result generated by the second common fragment set (step 205*c*) when the value of the coverage rate satisfies a predetermined value.

Or in other words, when the value of the coverage rate does not satisfy a predetermined value, the determining unit 103 changes the first seed table of the first reading sequence and the second seed table of the second reading sequence (i.e. continuing to perform comparisons of the specific seed length tables of the reading sequences according the conditional ordering schedule, until a value of the coverage rate of the specific seed length tables of the reading sequences does satisfy the predetermined value.) (repeating steps 205*a*, 205*b* and 205*d*) until the value of the coverage rate satisfies the predetermined value, and then generates the sequence comparison result generated by the second common fragment set (step 205*c*)

Figure 2C:
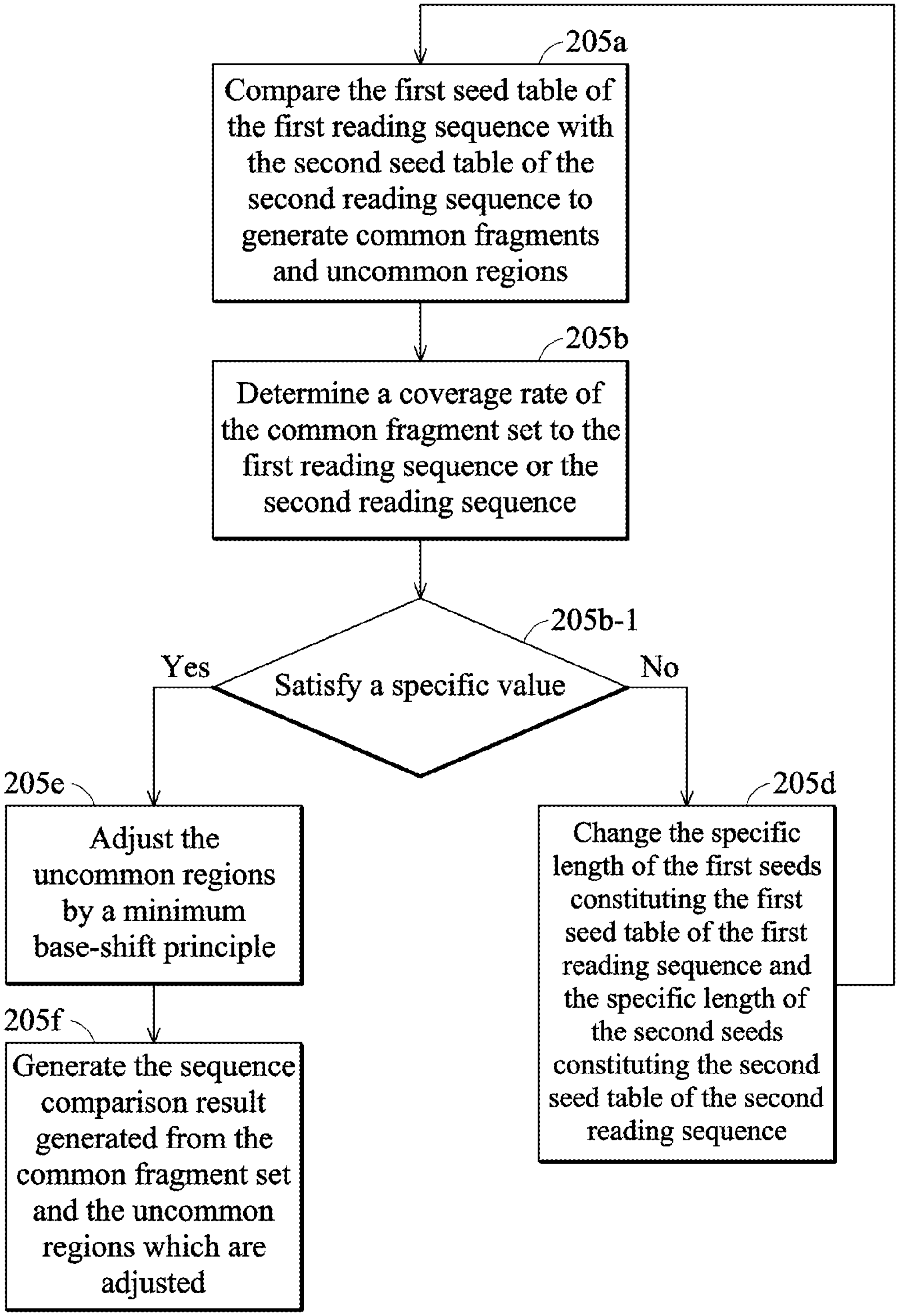
FIG. 2*c* shows a simplified flow chart of one embodiment of step 205 of the sequence calibration method for two reading sequences.

In another embodiment, see FIG. 2*c*, after determining a coverage rate of the common fragment set to the first reading sequence or the second reading sequence (step 205*b*), when the value of the coverage rate satisfies a predetermined value, the determining unit 103 adjusts the uncommon regions by the minimum base-shift principle (205*e*) and generates the sequence comparison result from the adjusted common fragment set and the uncommon regions (2050. The value of the predetermined value is not limited, and may be 80-95%, or preferably 95%.

The minimum base-shift principle may comprise the following procedures.

First, each uncommon region is divided into shorter seed sets, and the alignment position of each base of a first reading sequence and the second reading sequence of each shorter seed set is shifted, so that, when compared, the greatest amount of bases of the first reading sequence and the second reading sequence is equivalently aligned, wherein there is at least one alignment manner for each shorter seed set. Second, a positive score is given for each of the equivalently aligned bases of each shorter seed set and a negative score or no score is given for each of the non-equivalently aligned bases of each shorter seed set. Then, a total score for each shorter seed set of the uncommon region is calculated and the alignment manner of the shorter seed set of the uncommon region with the highest score is selected.

Furthermore, one of the conditions for adjusting the uncommon regions by the minimum base-shift principle may be, to make no adjustment, when a length of an uncommon region for the first reading sequence is different from the second reading. In another condition, adjusting the uncommon regions is performed in all cases. When adjusting the uncommon regions by the minimum base-shift principle, seeds may be used from long seed length (shorter than the specific length) to short seed length (shorter than the specific length), or when adjusting the uncommon regions by the minimum base-shift principle, short seeds (shorter than the specific length) may be used for locally optimum solution.

Comparatively, when the value of the coverage rate does not satisfy a predetermined value, the determining unit 103 changes the specific length of the first seeds constituting the first seed table of the first reading sequence and the specific length of the second seeds constituting the second seed table of the second reading sequence (i.e. changing the seed table of the first reading sequence with the specific seed length used in the comparison to the other seed table of the first reading sequence with the other specific seed and changing the seed table of the second reading sequence with the specific seed length used in the comparison to the other seed table of the second reading sequence with the other specific seed) (step 205*d*). Next, the determining unit 103 compares the first seed table constituted by the first seeds with the changed specific length with the second seed table constituted by the second seeds with the changed specific length at the uncommon regions (step 205*a*) to generate second common fragments and second uncommon regions, wherein the second common fragments and the first common fragment set constitute a second common fragment set. Subsequently, the determining unit 103 determines a coverage rate of the second common fragment set to the first reading sequence or the second reading sequence (step 205*b*). Then the determining unit 103 adjusts the uncommon regions by the minimum base-shift principle when the value of the coverage rate satisfies the predetermined value (205*e*) and generates the sequence comparison result generated by the second common fragment set and the uncommon regions which are adjusted (205*f*).

Or in other words, when the value of the coverage rate does not satisfy a predetermined value, the determining unit 103 changes of the first seed table of the first reading sequence and the second seed table of the second reading sequence (i.e. continuing to perform comparisons of the specific seed length tables of the reading sequences according the conditional ordering schedule, until a value of the coverage rate of the specific seed length tables of the reading sequences does satisfy the predetermined value.) (repeating steps 205*a*, 250*b* and 205*d*) until the coverage rate satisfies the predetermined value, and then adjusts the uncommon regions by the minimum base-shift principle when the value of the coverage rate satisfies the predetermined value (205*e*). The determining unit 103 generates the sequence comparison result generated by the second common fragment set and the uncommon regions which are adjusted (2050. Finally, the determining unit 103 outputs a calibrated sequence according to the sequence comparison result (step 207).

The first reading sequence and the second reading sequence may be read from a single sequence. In one embodiment, the single sequence is a concatenate sequence. The concatenate sequence may be read from a circle sequence, which has a known sequence part, such as a primer, and an unknown sequence part. The concatenate sequence may have primer-DNA repeat patterns. When the first reading sequence and the second reading sequence are read from a concatenate sequence having primer-DNA (DNA segment with connected primer) repeat patterns, first, the position and boundary of the primer of the concatenate are located. Second the position and boundary of the DNA are located, or "primer-DNA" pattern are located or "primer-DNA-primer" pattern are located. Then, the first reading sequence and the second reading sequence are obtained in the form of a "primer-DNA" pattern or "primer-DNA-primer" pattern.

More particularly, when the original sequence is a concatenate sequence having the primer-DNA (DNA segment with connected primer) repeat patterns, the seed tables of the primer and the seed tables sequence may be built first, and then the primer sequence is compared to possible positions in the concatenate sequences with the seed tables with longest seeds to locate the exact positions of the primers for retrieving the DNA segments. After that, the sequences of the DNA segments are obtained.

The sequence calibration method for a plurality of sequences is detailed in the following, in another aspect of the invention.

Figure 3A:
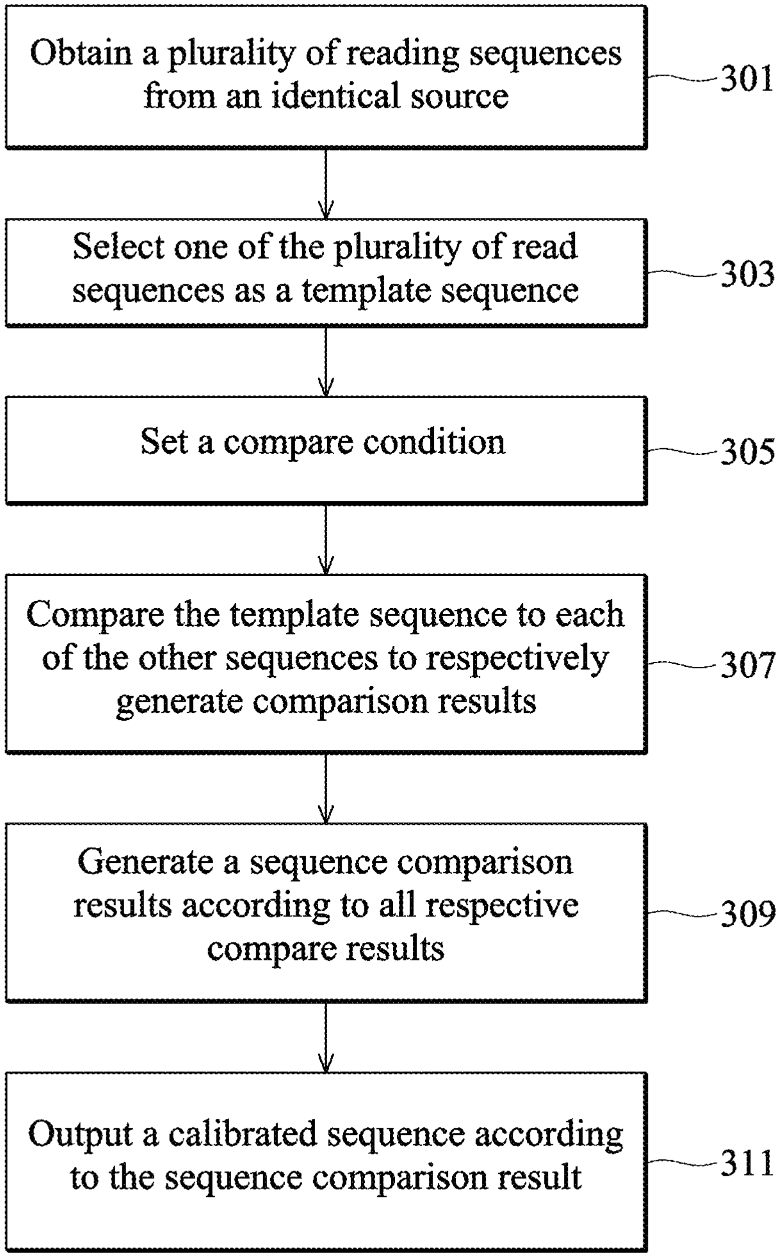
FIG. 3*a* shows a simplified flow chart of another embodiment of the sequence calibration method for a plurality of reading sequences.

Referring to FIG. 1 and FIG. 3, FIG. 1 shows a diagram of one embodiment of a sequence calibration device of the invention and FIG. 3 shows a simplified flow chart of one embodiment of the sequence calibration method performed by the device. The sequence calibration device 100 may comprises a receiving unit 101 and a determining unit 103. First, the receiving unit 101 obtains a plurality of reading sequences from an identical source by a receiving unit (step 301). Next, the determining unit 103 selects one of the plurality of reading sequences as a template sequence (step 303). After the template sequence is selected, the determining unit 103 sets a comparison condition (step 305). The method to select the template sequence from the plurality of reading sequences may comprise: (i) selecting the longest reading sequence among the plurality of reading sequences as the template sequence; (ii) selecting the reading sequence having a length which is closest to the average length of the plurality of reading sequences as the template sequence; (iii) selecting the reading sequence having a length which has the highest number of occurrence, among the plurality of reading sequences as the template sequence; or (iv) randomly selecting the reading sequence among the input sequences as the template sequence.

Figure 4:
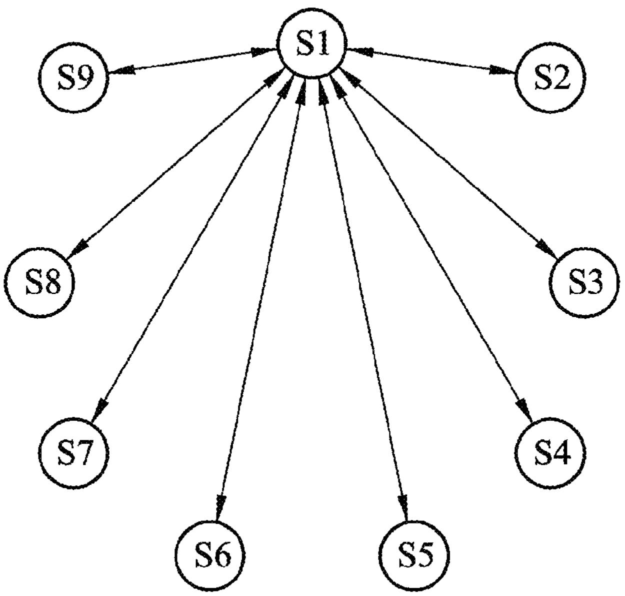
FIG. 4 shows a comparison method for the plurality of sequences of the invention.

After the template sequence is selected, the determining unit 103 compares the template sequence to each of the other sequences according to the comparison condition, to respectively generate comparison results (step 307). The comparison method for the plurality of sequences mentioned above is illustrated as FIG. 4. S1 to S9 represent different reading sequences, wherein S1 is selected as a template sequence.

Then, the determining unit 103 generates a sequence comparison result according to all respectively generated comparison results (step 309). Finally, the determining unit 103 outputs a calibrated sequence according to the sequence comparison result (step 311).

The determining unit 103 may set the comparison condition according to a first seed table of the template sequence and second seed tables for reading sequences which are not selected. The first seed table of the template sequence may comprise a plurality of first seeds with a specific length constituting a plurality of first seed sets with different seeding start sites and the second seed table of the reading sequence which is not selected may comprise a plurality of second seeds with a specific length constituting a plurality of second seed sets with different seeding start sites, wherein the specific length of the first seeds of the first seed table and the specific length of the second seeds of the second seed table are of the same specific length.

A seed table of a sequence may be built by the determining unit 103. Definitions for a seed, a seed set and a seed table are the same as mentioned above. The approach for building a seed table is also the same as mentioned above.

In addition, it is noted that the seed tables with different seed lengths (from the longest seed length need to the shortest seed length (2 mers)) of a sequence may be built at the same time. Or only a seed table with a specific length of a sequence may be built and the rest of the seed tables with other seed lengths may be built when needed. Moreover, the seed tables of two sequences which are to be compared are built first and the rest of the seed tables may be built when needed.

Figure 3B:
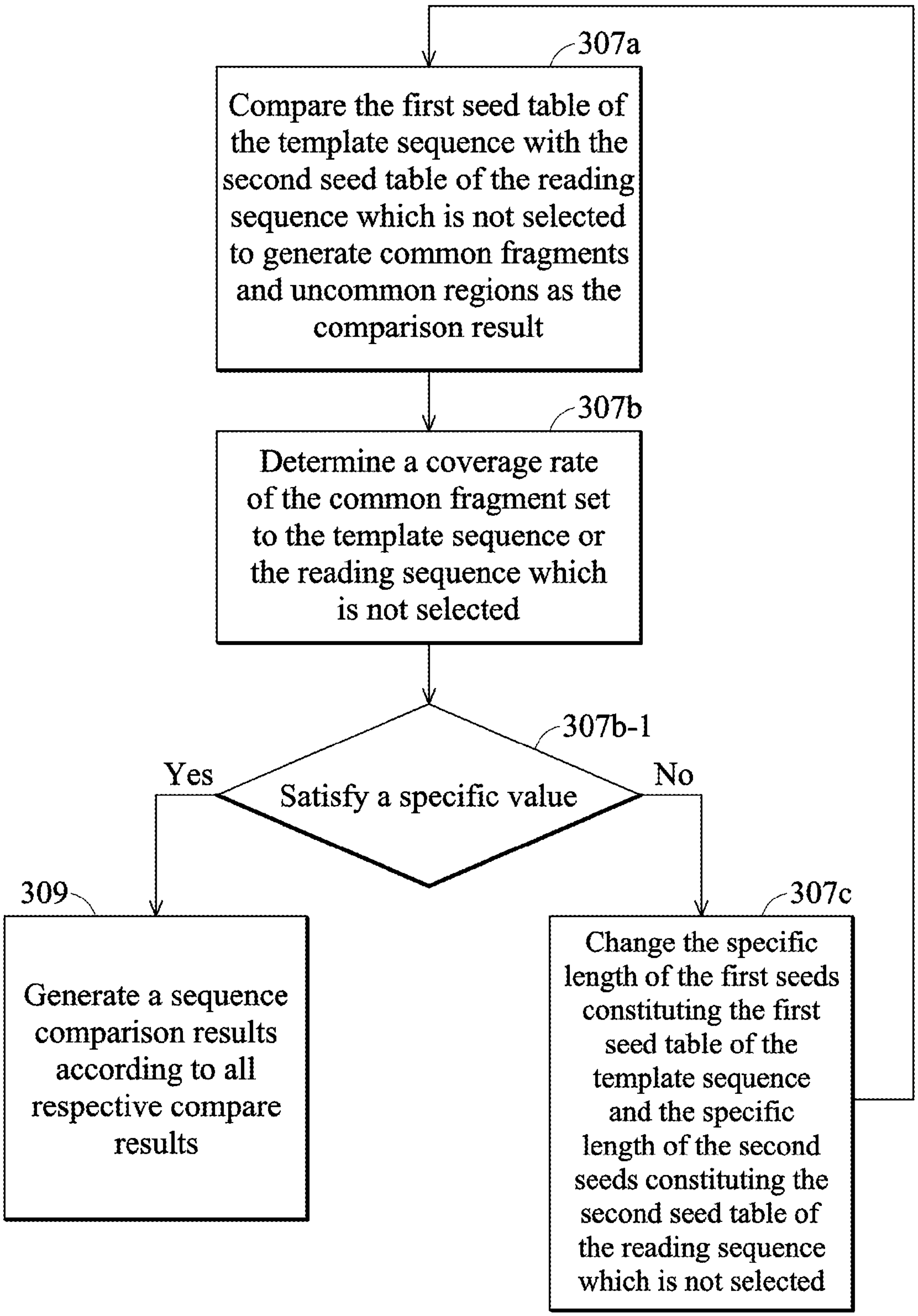
FIG. 3*b* shows a simplified flow chart of one embodiment of step 307 of FIG. 3*a*.

In one embodiment, see FIG. 3*b*, when the determining unit 103 compares the template sequence with the each of the other sequences according to the comparison condition, to respectively generate comparison results (step 307), in comparing the template sequence with one reading sequence which is not selected, the determining unit 103 may compare the first seed table of the template sequence with the second seed table of the reading sequence which is not selected to generate common fragments and uncommon regions as the comparison result (step 307*a*). One common fragment consists of at least one common seed and is between two uncommon regions without interruption, and the longer the common fragment is, the greater the amount of the common seed contained therein is. All common fragments generated by comparing the first seed table with the second seed table form a common fragment set. The common seed is defined as the seed of the template sequence and the seed of the reading sequence which is not selected, when the content of a seed of the template sequence and a seed of the reading sequence which is not selected at a corresponding region or a region close to the corresponding region are equivalent. After comparing the first seed table with the second seed table to generate common fragments and uncommon regions as the comparison result (step 307*a*), the determining unit 103 determines a coverage rate of the common fragment set to the template sequence or the reading sequence which is not selected (step 307*b*). When the value of the coverage rate satisfies a predetermined value, the determining unit 103 uses the common fragments to generating sequence comparison results according to all respectively generated comparison results (step 309). The value of the predetermined value is not limited, and may be 80-95%, or preferably 95%.

Comparatively, when the value of the coverage rate does not satisfy a predetermined value, the determining unit 103 changes the specific length of the first seeds constituting the first seed table of the template sequence and the specific length of the second seeds constituting the second seed table of the reading sequence which is not selected (i.e. continuing to perform comparisons of the specific seed length tables of the reading sequences according the conditional ordering schedule, until a value of the coverage rate of the specific seed length tables of the reading sequences does satisfy the predetermined value.) (step 307*c*). Next, the determining unit 103 compares the first seed table constituted by the first seeds with the changed specific length with the second seed table constituted by the second seeds with the changed specific length at the uncommon regions (step 307*a*) to generate a second common fragments and second uncommon regions, wherein the second common fragments and the first common fragment set constitute a second common fragment set, determines a coverage rate of the second common fragment set to the template sequence or the reading sequence which is not selected (step 307*b*) and uses the second common fragments to generate sequence comparison results according to all respectively generated comparison results (step 309) when the value of the coverage rate satisfies a predetermined value.

Or in other words, when the value of the coverage rate does not satisfy a predetermined value, the determining unit 103 changes the first seed table of the template sequence and the second seed table of the reading sequence which is not selected (i.e. continuing to perform comparisons of the specific seed length tables of the reading sequences according the conditional ordering schedule, until a value of the coverage rate of the specific seed length tables of the reading sequences does satisfy the predetermined value.) (repeating steps 307*a*, 307*b* and 307*c*) until the coverage rate satisfies the predetermined value, and then uses the second common fragments to generate a sequence comparison results according to all respectively generated comparison results (step 309).

Figure 3C:
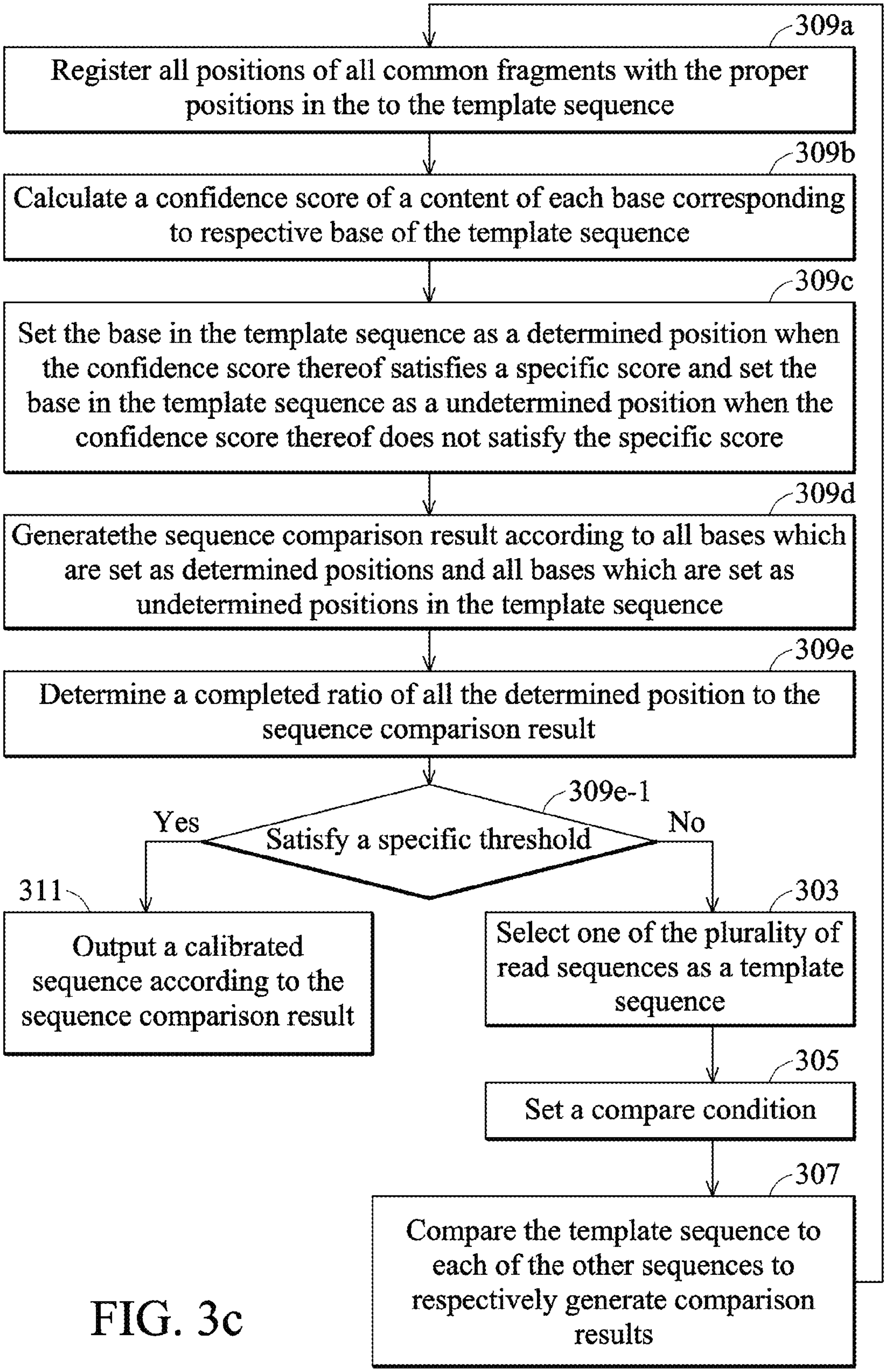
FIG. 3*c* shows a simplified flow chart of one embodiment of step 309 of FIG. 3*a*.

Procedures for generating sequence comparison results according to all respectively generated comparison results (step 309) may comprise the following (see FIG. 3*c*).

First, the determining unit 103 registers all positions of all common fragments obtained from generating sequence comparison results according to all respectively generated comparison results (step 307) with the proper positions in the template sequence (step 309*a*). Then, the determining unit 103 calculates a confidence score of a content of each base corresponding to the respective bases of the template sequence according to all common fragments (step 309*b*). Next, the determining unit 103 sets the base in the template sequence as a determined position when the confidence score thereof satisfies a specific score and sets the base in the template sequence as a undetermined position when the confidence score thereof does not satisfy a specific score (step 309*c*).

Figure 5:
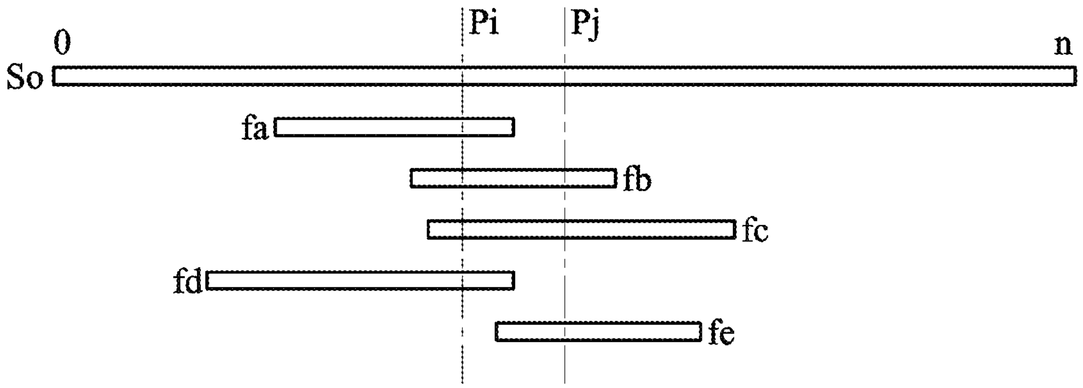
FIG. 5 shows an illustration for calculating a confidence score of a content of each position.

An illustration for calculating a confidence score of a content of each position is shown in FIG. 5

Pi and Pj are two positions corresponding to the template. fa-fe are common fragments generated from comparing two sequences. The confidence scores of fa-fe are a-e, respectively. The confidence score of each position is represented by $$C_P = \sum_x fx.$$

The confidence scores of contents of Pi and Pj are represented by $C_{pi}$=(a+b+c+d) and $C_{pj}$=(b+c+e), respectively.

After, the determining unit 103 generates the sequence comparison result according to all bases which are set as determined positions and all bases which are set as undetermined positions in the template sequence (step 309*d*). Subsequently, the determining unit 103 determines a completed ratio for all of the determined positions to the sequence comparison result (step 309*e*). Finally, when the completed ratio satisfies a specific threshold, the determining unit 103 uses the sequence comparison result to output a calibrated sequence according to the sequence comparison result (step 311). The value of the specific threshold is not limited, and may be 80-95%, or preferably 95%.

Comparatively, when the completed ratio does not satisfy a predetermined value, the determining unit 103 repeats the steps 303, 305 and 307, wherein a new template sequence is selected from the plurality of reading sequences without the first template and the first template is stopped from being compared, and wherein new common fragments and new uncommon regions are generated from comparing the new template sequence with the other reading sequences. After that, the determining unit 103 registers all positions of all new common fragments with the proper positions in the sequence comparison result (step 309*a*), calculates a confidence score of a content of each undetermined positions corresponding to the sequence comparison result according to the new common fragments which correspond to the positions of the undetermined positions (step 309*b*). Then, the determining unit 103 sets each base of the undetermined positions in the sequence comparison result as a new determined position when the confidence score thereof satisfies a specific score and still set the base in the undetermined positions as a undetermined position when the confidence score thereof does not satisfy a specific score (step 309*c*) and generates a new sequence comparison result by the sequence comparison result and the new determined positions (step 309*d*). Next, the determining unit 103 determines a completed ratio of all the determined positions to the new sequence comparison result. Finally, when the completed ratio satisfies the specific threshold, the new sequence comparison result is used to output a calibrated sequence (step 311). Finally, the determining unit 103 outputs a calibrated sequence according to new sequence comparison result.

Furthermore, in still other embodiment, the determining unit 103 may adjust the undetermined positions of the sequence comparison result by a minimum base-shift principle before outputting a calibrated sequence (step 311). The procedures and conditions for the minimum base-shift principle are the same as that mentioned above.

Figure 6:
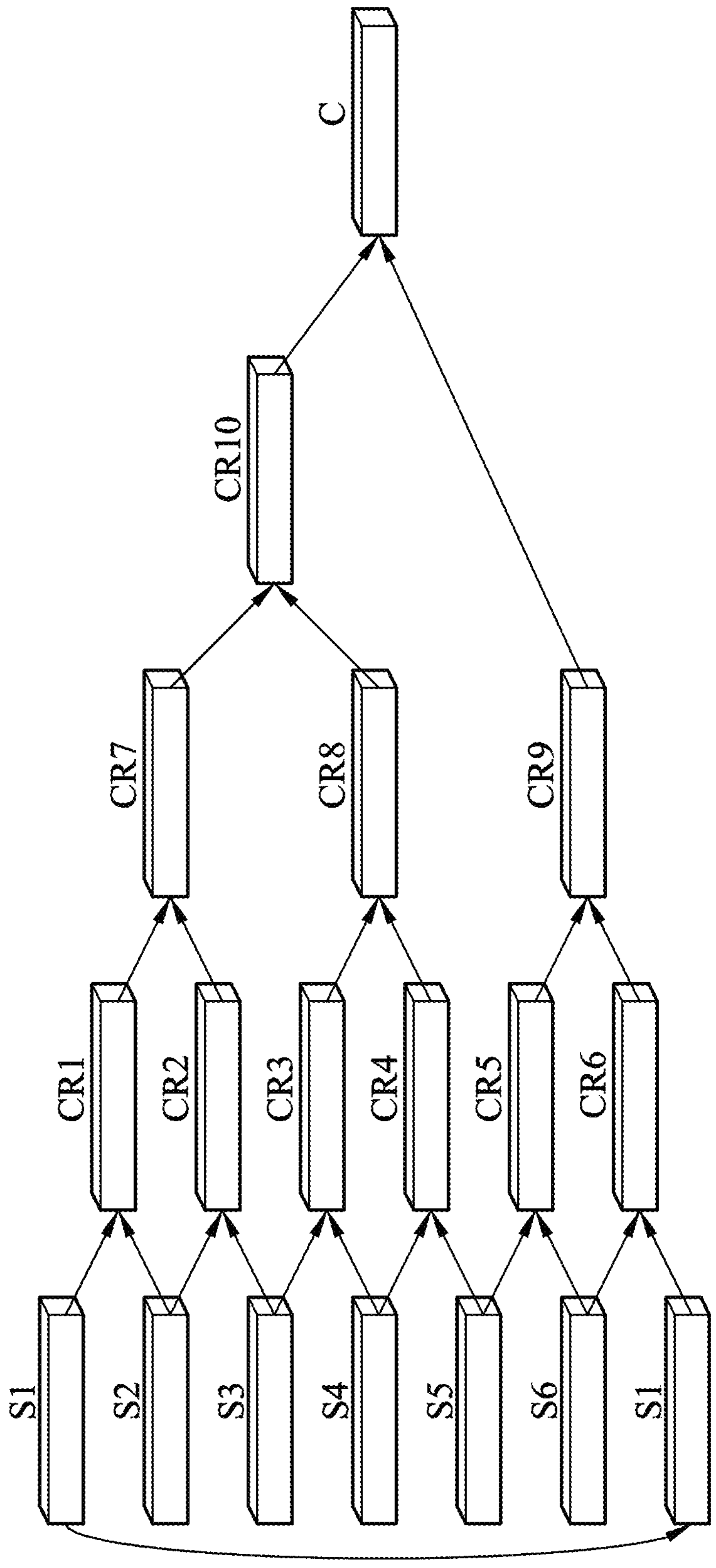
FIGS. 6-8 shows other comparison methods for the plurality of sequences of the invention.
Figure 7:
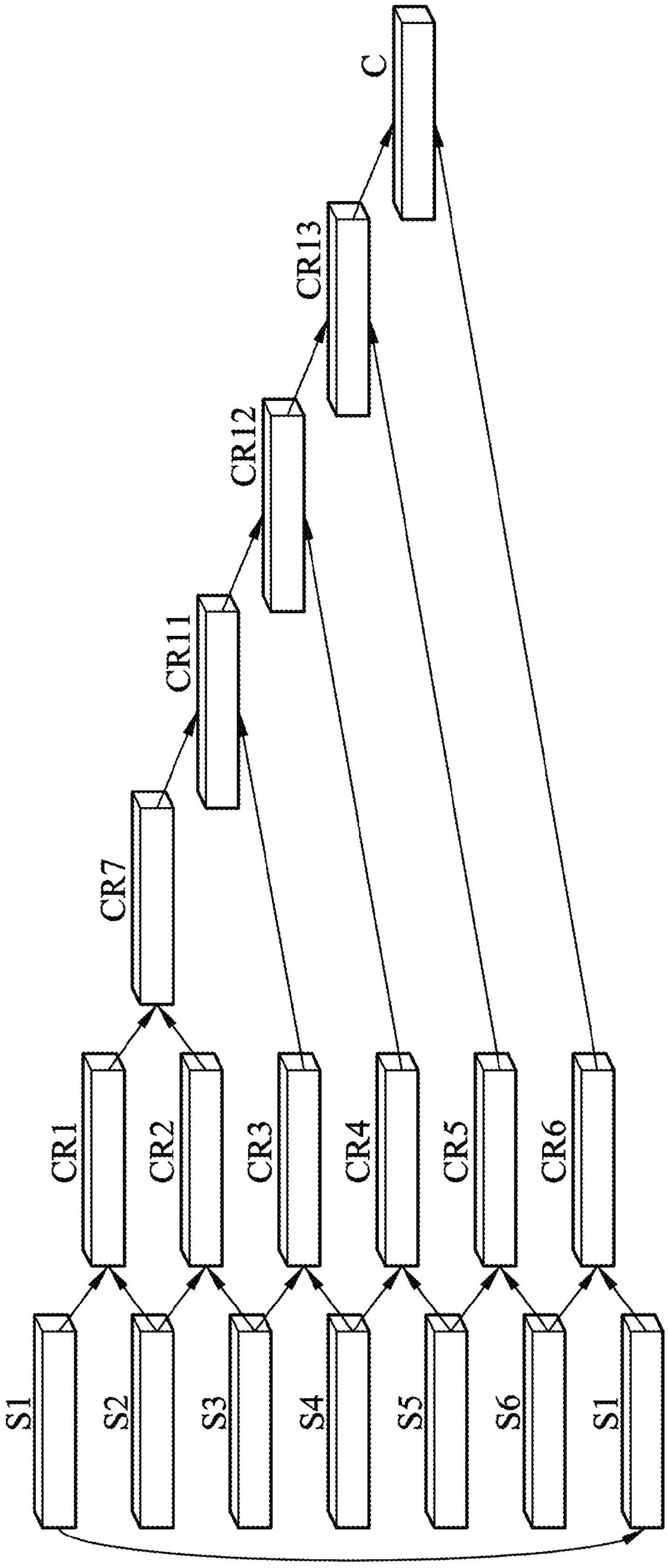
Figure 8:
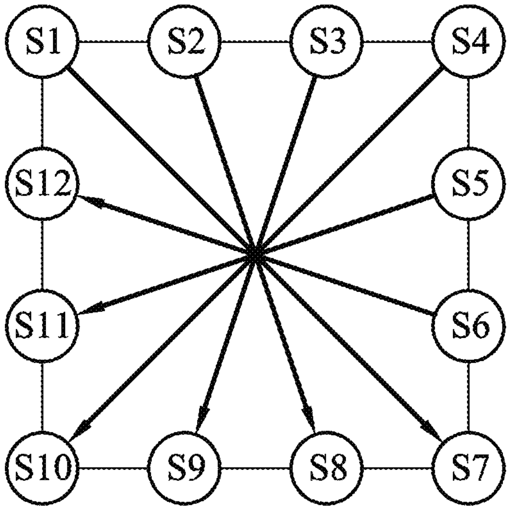

In still another aspect, there are other methods for comparison of the plurality of sequences in the sequence calibration method of the invention. See FIGS. 6-8, wherein FIGS. 6-8 show different methods for comparing the plurality of sequences in the sequence calibration method of the invention.

S1 to S12 represent different reading sequences. CR1 to CR13 represent different sequence comparison results generated from different comparison orders. C represents an outputted calibrated sequence.

Moreover, the plurality of reading sequences may be read from a single sequence. In one embodiment, the single sequence is a concatenate sequence. The concatenate sequence may be read from a circle sequence, which has a known sequence part, such as a primer, and an unknown sequence part. The concatenate sequence may have primer-DNA repeat patterns. The method to retrieve DNA fragments is similar to that which was mentioned above.

EXAMPLE

Example 1

I. Generating a Sequence

First, this invention uses a 60-base long DNA sequence as its input to randomly generate five different sequences. The variation of the sequences is the error probability of the random generator, i.e. 10%. The similarities of the five sequences are between 79% and 89%.

The original content of the sequence is:

```
                                          (SEQ ID. No.: 1)
GATACGTAGGGTGGCTAAGATACTGTTGTTCAGACACATCCGCCCGCCT

TCTCTGGCGGG
```

II. Input Multiple DNA Sequences

The contents of the five randomly generated sequences are:

```
                                          (SEQ ID. No.: 2)
1: CATACGTAGGGTGGCTAAGATACTTTTGTTCAGACACATCCCCCCC
CTTCTCTGGCGGG

                                          (SEQ ID. No.: 3)
2: TATGCGTAGGGTGGCTAAGATACTTTTGTTCAGATACTCCAGCCCG
CCTTCGCTGGCGGG

                                          (SEQ ID. No.: 4)
3: GATACGTAGGGGGGCTACGATACTTTAGTTCAGACACAACCGCCCG
TCTTCTCTGGCGGG

                                          (SEQ ID. No.: 5)
4: GATACGTAGGGTGGCTAAGATACTGTGTTCAGACACAACCGCCCGC
CTTCTCTGGCGGG
```

-continued

```
                                   (SEQ ID. No.: 6)
5: GATACGTAGGGTGGCTAAGATACTGTAGTTCAGACACATCCGCACG
CCTACTCTGGCTGG
```

III. Pairwise Comparisons of N Multiple Sequences

See FIG. 9*a*, wherein the invention compares N sequences with their prebuilt seed tables. Sequence #1 (selected as a template sequence) is compared with sequence #2 and then with sequence #3, and so on to determine common sequence fragments. The symbols "*" indicate the common fragments between each pair of sequences. The circles indicate the base deletion position after the simple fragment is aligned.

IV. Global Registration of all Common Fragments in N Sequences

See FIG. 9*b*. The bottom line in FIG. 9*b* is called a "sequence comparison result". In this sequence comparison result, the alphabetic characters indicate positions that are determined and the symbols "?" indicate undetermined positions. The alphabetic characters are the final content of the sequence comparison result. The circle indicates one undetermined area.

V. Pairwise Comparisons of (N-1) Sequences

See FIG. 9*c*, wherein after previous operations, there are still some undetermined positions. Thus, the second iteration, step 5 to step 6, is preformed.

The bottom line in the graph is called a "sequence comparison result". In this sequence comparison result, the alphabetic characters indicate positions that are determined and the symbols "?" indicate undetermined positions. The dotted line circle indicates one possible deletion.

VI. Pairwise Comparisons of (N-1) Sequences

See FIG. 9*d*, wherein the invention compares N-1 sequences with their prebuilt seed tables. Sequence #2 is compared with sequence #3 and then with sequence #4, and so on, to determine common sequence fragments. The symbols "*" indicate the common fragments between each pair of sequences. The dotted line circle indicates one possible deletion.

VII. Global Registration of all Common Fragments in (N-1) Sequences

Figure 9E:
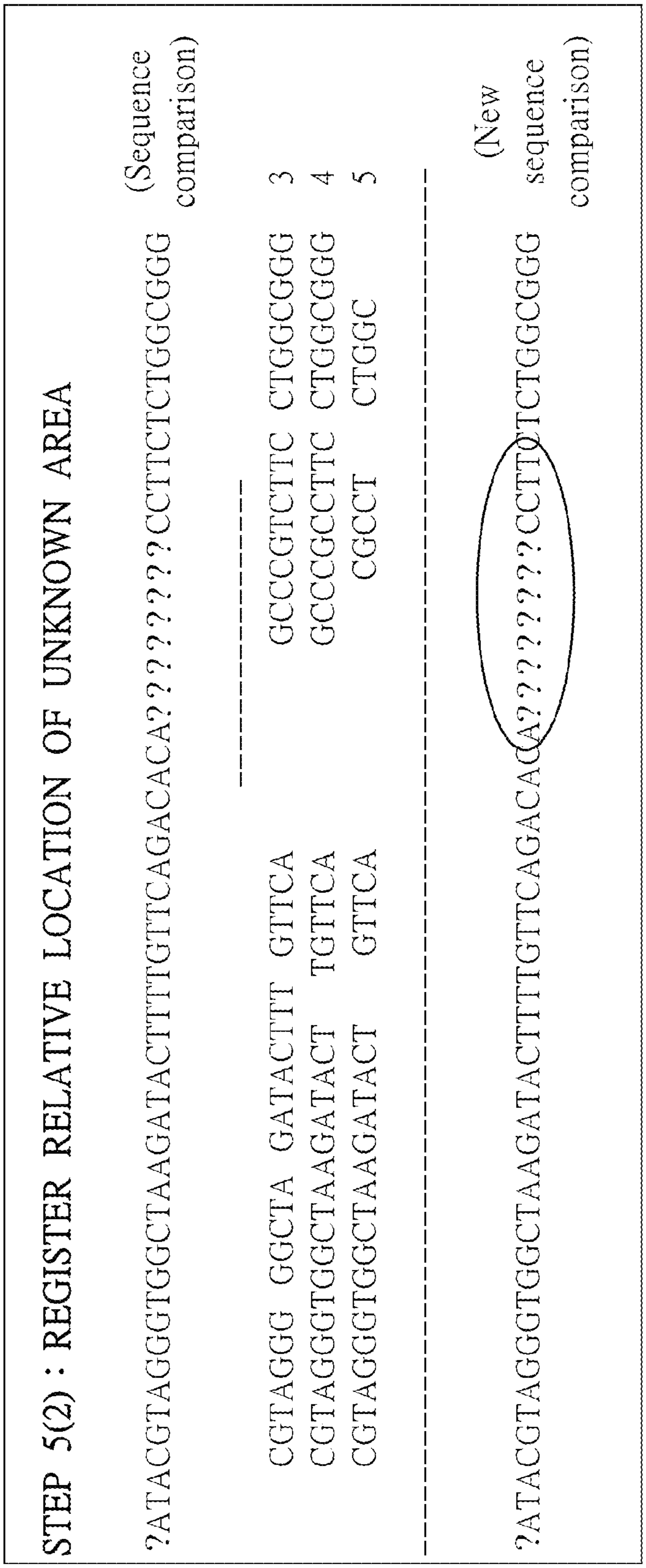

See FIG. 9*e*, wherein the bottom line in the graph is called a "New sequence comparison result". In this sequence comparison result, the alphabetic characters indicate positions that are determined, but not the final results, and the symbols "?" indicate some undetermined positions. The dotted line circle indicates one undetermined area.

VIII. Adjustment of the Undetermined Area

See FIG. 9*f*, wherein the bottom line in the graph is the registered result. As previously mentioned, the invention applies a scoring method for every base in the result. Thus, each base in the new sequence comparison result has a confidence score. The score of each base is related to the registered fragment position in the new sequence comparison result and their length. The symbols "◎" indicate the possible indel positions.

IX. Output of One Adjusted DNA Sequence

See FIG. 9*g*, wherein the graph shows the adjusted result. The invention use different colors to distinguish the confidence level. The symbols "*" indicate the mismatched positions between the calibrated sequence and the original sequence.

Example 2

I. Generating the Sequence

First, this invention uses a 100-base long DNA sequence (digested from gi|4210524|dbj|AB005269.1) as its input to randomly generate 10 different sequences. The variation of the sequences is the error probability of the random generator, i.e. 10%. The similarities of the five sequences are between 79% and 89%.

>gi|4210524|dbj|AB005269.1|AB00526S03 Mus musculus wagneri gene for 105-kDa heat shock protein, exon 3

```
                                   (SEQ ID. No.: 10)
TTTGAGTCTGCCCCAAAGTCTGATGACCCATTGCCTTTCCTTGTGGCAT

TTTCCATAGAAGAAAGTACAGTAGGAGTATCCATTCATGGAAAATCGAG

GA
```

II. Input Multiple DNA Sequences

The contents of the nine randomly generated sequences are shown in FIG. 10*a*

III. Pairwise Comparisons of N Multiple Sequences

Figure 10B:
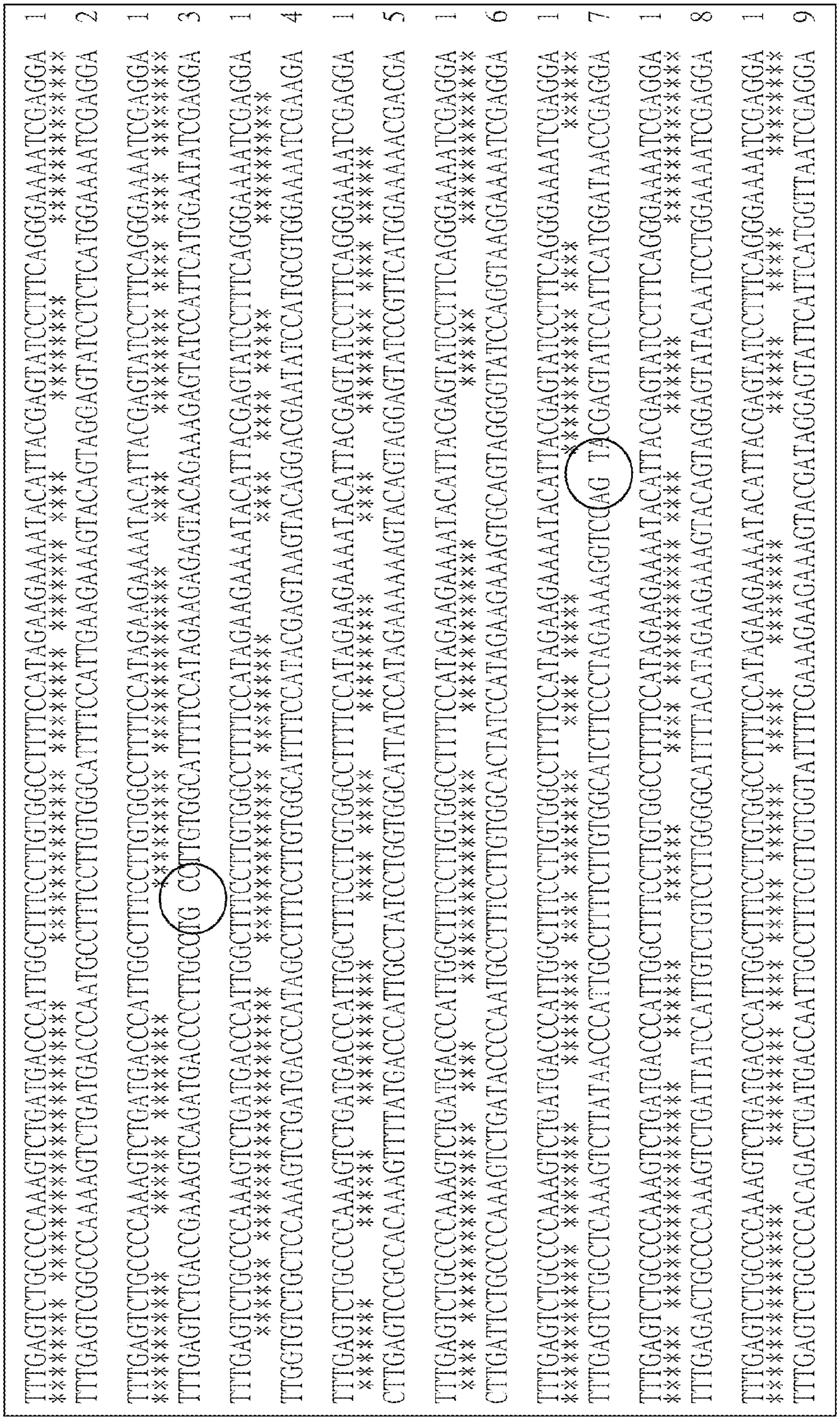

See FIG. 10*b*, wherein the invention compares N sequences with their prebuilt seed tables. Sequence #1 is compared with sequence #2 and then with sequence #3, and so on, to determine common sequence fragments. The symbols "*" indicate the common fragments between each pair of sequences. The circles indicate the position of possible base deletion.

IV. Global Registration of all Common Fragments in N Sequences

See FIG. 10*c*, wherein the last line in the graph is called a "sequence comparison result". In this sequence comparison result, the alphabetic characters indicate positions that are determined and the symbols "?" indicate undetermined positions. The alphabetic characters are the final content of the sequence comparison result.

V. Locating Undetermined Positions in the N Sequences

See FIG. 10*d*. The last line in the graph is called a "sequence comparison result". In this sequence comparison result, the symbols "?" indicate undetermined positions. The dotted line circles indicate some possible deletions.

VI. Adjustment of the Undetermined Area

See FIG. 10*e*, wherein the bottom line in the graph is the registered result. As previously mentioned, the invention applies a scoring method for every base in this result. Thus, each base in the sequence comparison result has a confidence score. The score of each base is related to the registered fragment position in the sequence comparison result and their length. The symbols "◎" indicate the possible indel positions.

VII. Output of One Adjusted DNA Sequence

See FIG. 10*f*, wherein the graph shows the adjusted result and the complete match between the calibrated sequence and the original sequence.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A sequence calibration method, comprising:

(a) sequencing a nucleic acid;

(b) obtaining a first reading sequence and a second reading sequence from an identical source;

(c) setting a comparison condition; and (d) comparing the first reading sequence with the second reading sequence according to the comparison condition to generate a sequence comparison result; and (e) outputting a calibrated sequence according to the sequence comparison result, wherein the comparison condition is set according to a first seed table of the first reading sequence and a second seed table of the second reading sequence, wherein the first seed table of the first reading sequence comprises a plurality of first seeds with a specific length constituting a plurality of first seed sets with different seeding start sites and the second seed table of the second reading sequence comprises a plurality of second seeds with a specific length constituting a plurality of second seed sets with different seeding start sites, and wherein the specific length of the first seeds of the first seed table and the specific length of the second seeds of the second seed table are of the same specific length.

2. The sequence calibration method as claimed in claim 1, wherein the first reading sequence and the second reading sequence are from a single sequence.

3. The sequence calibration method as claimed in claim 2, wherein the single sequence is a concatenate sequence.

4. The sequence calibration method as claimed in claim 3, wherein the concatenate sequence has primer-DNA repeat patterns.

5. The sequence calibration method as claimed in claim 1, wherein the specific length of the first seeds or the second seeds is a positive integer of at least than 2.

6. The sequence calibration method as claimed in claim 1, wherein the specific length of the first seeds or the second seeds is a positive integer of 3-9.

7. The sequence calibration method as claimed in claim 1, wherein a basis for choosing the specific length of the first seeds or the second seeds may comprise experiences of a user, the length of the sequence or the accuracy of a prior calibrated sequence from sequence calibration method.

8. The sequence calibration method as claimed in claim 1, wherein the step (d) comprises:

comparing the first seed table with the second seed table to generate common fragments and uncommon regions, wherein one common fragment consists of at least one common seed and is between two uncommon regions without interruption, and the longer the common fragment is, the greater the amount of the common seed contained therein is, and wherein all common fragments generated by comparing the first seed table with the second seed table form a common fragment set;

determining a coverage rate of the common fragment set to the first reading sequence or the second reading sequence; and generating the sequence comparison result from the common fragment set when the value of the coverage rate satisfies a predetermined value.

9. The sequence calibration method as claimed in claim 8, when the value of the coverage rate does not satisfy the predetermined value, further comprising:

changing the specific length of the first seeds constituting the first seed table of the first reading sequence and the specific length of the second seeds constituting the second seed table of the second reading sequence;

comparing the first seed table constituted by the first seeds with the changed specific length with the second seed table constituted by the second seeds with the changed specific length at the uncommon regions to generate a second common fragments and second uncommon regions, wherein the second common fragments and the first common fragment set constitute a second common fragment set;

determining a coverage rate of the second common fragment set to the first reading sequence or the second reading sequence; and generating the sequence comparison result generated by the second common fragment set when the value of the coverage rate satisfies the predetermined value.

10. The sequence calibration method as claimed in claim 8, further comprising:

continually changing the specific length when the coverage rate does not satisfy the predetermined value until the coverage rate satisfies the predetermined value.

11. The sequence calibration method as claimed in claim 8, wherein the common seed is defined as the seed of the first reading sequence and the seed of the second reading sequence, when the content of a seed of the first reading sequence and a seed of the second reading sequence at a corresponding region or a region close to the corresponding region are equivalent.

12. The sequence calibration method as claimed in claim 1, wherein the step (d) comprises:

comparing the first seed table with the second seed table to generate common fragments and uncommon regions, wherein one common fragment consists of at least one common seed and is between two uncommon regions without interruption, and the longer the common fragment is, the greater the amount of the common seed contained therein is, and wherein all common fragments generated by comparing the first seed table with the second seed table form a common fragment set;

determining a coverage rate of the common fragment set to the first reading sequence or the second reading sequence;

adjusting the uncommon regions by the minimum base-shift principle when the value of the coverage rate satisfies a predetermined value; and generating the sequence comparison result from the adjusted common fragment set and the uncommon regions.

13. The sequence calibration method as claimed in claim 12, when the value of the coverage rate does not satisfy the predetermined value, further comprising:

changing the specific length of the first seeds constituting the first seed table of the first reading sequence and the specific length of the second seeds constituting the second seed table of the second reading sequence;

comparing the first seed table constituted by the first seeds with the changed specific length with the second seed table constituted by the second seeds with the changed specific length at the uncommon regions to generate a second common fragments and second uncommon regions, wherein the second common fragments and the first common fragment set constitute a second common fragment set;

determining a coverage rate of the second common fragment set to the first reading sequence or the second reading sequence; and adjusting the uncommon regions by the minimum base-shift principle when the value of the coverage rate satisfies the predetermined value; and generating the sequence comparison result from the adjusted common fragment set and the uncommon regions.

14. The sequence calibration method as claimed in claim 12, further comprising:

continually changing the specific length of the first seeds constituting the first seed table of the first reading sequence and the specific length of the second seeds constituting the second seed table of the second reading sequence when the coverage rate does not satisfy the predetermined value until the coverage rate until the coverage rate satisfies the predetermined value.

15. The sequence calibration method as claimed in claim 12, wherein the common seed is defined as the seed of the first reading sequence and the seed of the second reading sequence, when the content of a seed of the first reading sequence and a seed of the second reading sequence at a corresponding region or a region close to the corresponding region are equivalent.

16. The sequence calibration method as claimed in claim 12, wherein the minimum base-shift principle comprises:

dividing each uncommon region into shorter seed sets, and shifting the alignment position of each base of a first reading sequence and the second reading sequence of each shorter seed set, so that, when compared, the greatest amount of bases of the first reading sequence and the second reading sequence is equivalently aligned, wherein there is at least one alignment manner for each shorter seed set;

giving a positive score for each of the equivalently aligned bases of each shorter seed set and giving a negative score for each of the non-equivalently aligned bases of each shorter seed set; and calculating a total score for each shorter seed set of the uncommon region, and selecting the alignment manner of the shorter seed set of the uncommon region with the highest score.

17. A sequence calibration method, comprising:

(a) sequencing a nucleic acid;

(b) obtaining a plurality of reading sequences from an identical source;

(c) selecting one of the plurality of reading sequences as a template sequence;

(d) setting a comparing condition;

(e) comparing the template sequence to each of the other sequences according to the comparison condition, to respectively generate comparison results by the determining unit;

(f) generating a sequence comparison result according to all respectively generated comparison results; and (g) outputting a calibrated sequence according to the sequence comparison result, wherein the comparison condition is set according to a first seed table of the template sequence and second seed tables for reading sequences which are not selected as the template sequence, wherein the first seed table of the template sequence comprises a plurality of first seeds with a specific length constituting a plurality of first seed sets with different seeding start sites and the second seed table of the reading sequence which is not selected comprises a plurality of second seeds with a specific length constituting a plurality of second seed sets with different seeding start sites, and wherein the specific length of the first seeds of the first seed table and the specific length of the second seeds of the second seed table are of the same specific length.

18. The sequence calibration method as claimed in claim 17, wherein the plurality of reading sequences are from a single sequence.

19. The sequence calibration method as claimed in claim 18, wherein the single sequence is a concatenate sequence.

20. The sequence calibration method as claimed in claim 19, wherein the concatenate sequence has primer-DNA repeat patterns.

21. The sequence calibration method as claimed in claim 17, wherein the specific length of the first seeds or the second seeds is a positive integer of at least 2.

22. The sequence calibration method as claimed in claim 17, wherein the specific length of the first seeds or the second seeds is a positive integer of 3-9.

23. The sequence calibration method as claimed in claim 17, wherein a basis for choosing the specific length of the first seeds or the second seeds may comprise experiences of a user, the length of the sequence or the accuracy of a prior calibrated sequence from sequence calibration method.

24. The sequence calibration method as claimed in claim 17, wherein comparing the template sequence with one reading sequence which is not selected in the step (e) comprises:

comparing the first seed table with the second seed table to generate common fragments and uncommon regions as the comparison result, wherein one common fragment consists of at least one common seed and is between two uncommon regions without interruption, and the longer the common fragment is, the greater the amount of the common seed contained therein is, and wherein all common fragments generated by comparing the first seed table with the second seed table form a common fragment set;

determining a coverage rate of the common fragment set to the template sequence or the reading sequence which is not selected; and using the common fragments in the step (f) when the value of the coverage rate satisfies a predetermined value.

25. The sequence calibration method as claimed in claim 24, further comprising:

continually changing the specific length of the first seeds constituting the first seed table of the first reading sequence and the specific length of the second seeds constituting the second seed table of the second reading sequence when the coverage rate does not satisfy the predetermined value until the coverage rate until the coverage rate satisfies the predetermined value.

26. The sequence calibration method as claimed in claim 24, wherein the step (f) further comprises:

registering all positions of all common fragments obtained from the step (e) with the proper positions in the template sequence; and calculating a confidence score for the content of each base corresponding to respective template sequence bases according to all common fragments;

setting the base in the template sequence as a determined position when the confidence score for the content of each base corresponding to respective template sequence bases satisfies a specific score and setting the base in the template sequence as an undetermined position when the confidence score for the content of each base corresponding to respective template sequence bases does not satisfy a specific score;

generating the sequence comparison result according to all bases which are set as determined positions and all bases which are set as undetermined positions in the template sequence;

determining a completed ratio for all of the determined positions to the sequence comparison result; and using the sequence comparison result in the step (g) when the completed ratio satisfies a specific threshold.

27. The sequence calibration method as claimed in claim 26, when the value of the coverage rate does not satisfy the predetermined value, further comprising:

repeating the step (d)-(e), wherein a new template sequence is selected from the plurality of reading sequences without the first template and the first template is stopped from being compared, and wherein the new common fragments and the new uncommon regions are generated from comparing the new template sequence with the other reading sequences;

registering all positions of all new common fragments with the proper positions in the sequence comparison result; and calculating a confidence score for the content of each undetermined positions corresponding to respective bases of the sequence comparison result according to the new common fragments which correspond to the positions of the undetermined positions;

setting each base of the undetermined positions in the sequence comparison result as a new determined position when the confidence score thereof satisfies a specific score, and still setting the base in the undetermined positions as a undetermined position when the confidence score thereof does not satisfy a specific score;

generating a new sequence comparison result according to the sequence comparison result and the new determined positions;

determining a completed ratio of all the determined positions to the new sequence comparison result; and using the new sequence comparison result in the step (g) when the completed ratio satisfies a specific threshold.

28. The sequence calibration method as claimed in claim 26, further comprising adjusting the undetermined positions of the sequence comparison result by a minimum base-shift principle before the step (g).

* * * * *

SEQUENCE LISTING

<160> NUMBER OF SEQ ID NOS: 21

<210> SEQ ID NO 1
<211> LENGTH: 60
<212> TYPE: DNA
<213> ORGANISM: Artificial Sequence
<220> FEATURE:
<223> OTHER INFORMATION: Randomly generated sequence obtained from
computer processing

<400> SEQUENCE: 1
gatacgtagg gtggctaaga tactgttgtt cagacacatc cgcccgcctt ctctggcggg 60

<210> SEQ ID NO 2
<211> LENGTH: 59
<212> TYPE: DNA
<213> ORGANISM: Artificial Sequence
<220> FEATURE:
<223> OTHER INFORMATION: Randomly generated sequence obtained from
computer processing

<400> SEQUENCE: 2
catacgtagg gtggctaaga tacttttgtt cagacacatc cccccccttc tctggcggg 59

<210> SEQ ID NO 3
<211> LENGTH: 60
<212> TYPE: DNA
<213> ORGANISM: Artificial Sequence
<220> FEATURE:
<223> OTHER INFORMATION: Randomly generated sequence obtained from
computer processing

<400> SEQUENCE: 3
tatgcgtagg gtggctaaga tacttttgtt cagatactcc agcccgcctt cgctggcggg 60

<210> SEQ ID NO 4
<211> LENGTH: 60
<212> TYPE: DNA
<213> ORGANISM: Artificial Sequence
<220> FEATURE:
<223> OTHER INFORMATION: Randomly generated sequence obtained from
computer processing

<400> SEQUENCE: 4
gatacgtagg ggggctacga tactttagtt cagacacaac cgcccgtctt ctctggcggg 60

<210> SEQ ID NO 5
<211> LENGTH: 59
<212> TYPE: DNA
<213> ORGANISM: Artificial Sequence
<220> FEATURE:
<223> OTHER INFORMATION: Randomly generated sequence obtained from
computer processing

<400> SEQUENCE: 5
gatacgtagg gtggctaaga tactgtgttc agacacaacc gcccgccttc tctggcggg 59

<210> SEQ ID NO 6
<211> LENGTH: 60
<212> TYPE: DNA
<213> ORGANISM: Artificial Sequence
<220> FEATURE:
<223> OTHER INFORMATION: Randomly generated sequence obtained from
computer processing

<400> SEQUENCE: 6

-continued gatacgtagg gtggctaaga tactgtagtt cagacacatc cgcacgccta ctctggctgg 60

<210> SEQ ID NO 7
<211> LENGTH: 60
<212> TYPE: DNA
<213> ORGANISM: Artificial Sequence
<220> FEATURE:
<223> OTHER INFORMATION: Randomly generated sequence obtained from
computer processing
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (39)..(46)
<223> OTHER INFORMATION: n is a, c, g, or t

<400> SEQUENCE: 7
natacgtagg gtggctaaga tacttttgtt cagacacann nnnnnncctt ctctggcggg 60

<210> SEQ ID NO 8
<211> LENGTH: 60
<212> TYPE: DNA
<213> ORGANISM: Artificial Sequence
<220> FEATURE:
<223> OTHER INFORMATION: Randomly generated sequence obtained from
computer processing
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (39)..(41)
<223> OTHER INFORMATION: n is a, c, g, or t

<400> SEQUENCE: 8
natacgtagg gtggctaaga tacttttgtt cagacacann ngcccgcctt ctctggcggg 60

<210> SEQ ID NO 9
<211> LENGTH: 58
<212> TYPE: DNA
<213> ORGANISM: Artificial Sequence
<220> FEATURE:
<223> OTHER INFORMATION: Randomly generated sequence obtained from
computer processing

<400> SEQUENCE: 9
gtacgtaggg tggctaagat acttttgttc agacacaccg cccgccttct ctggcggg 58

<210> SEQ ID NO 10
<211> LENGTH: 100
<212> TYPE: DNA
<213> ORGANISM: Mus musculus wagneri

<400> SEQUENCE: 10
tttgagtctg ccccaaagtc tgatgaccca ttgcctttcc ttgtggcatt ttccatagaa 60
gaaagtacag taggagtatc cattcatgga aaatcgagga 100

<210> SEQ ID NO 11
<211> LENGTH: 100
<212> TYPE: DNA
<213> ORGANISM: Artificial Sequence
<220> FEATURE:
<223> OTHER INFORMATION: Randomly generated sequence obtained from
computer processing

<400> SEQUENCE: 11

-continued tttgagtctg ccccaaagtc tgatgaccca ttggctttcc ttgtggcctt ttccatagaa 60
gaaaatacat tacgagtatc ctttcaggga aaatcgagga 100

<210> SEQ ID NO 12
<211> LENGTH: 100
<212> TYPE: DNA
<213> ORGANISM: Artificial Sequence
<220> FEATURE:
<223> OTHER INFORMATION: Randomly generated sequence obtained from computer processing

<400> SEQUENCE: 12
tttgagtcgg cccaaaagtc tgatgaccca atgcctttcc ttgtggcatt ttccattgaa 60
gaaagtacag taggagtatc ctctcatgga aaatcgagga 100

<210> SEQ ID NO 13
<211> LENGTH: 99
<212> TYPE: DNA
<213> ORGANISM: Artificial Sequence
<220> FEATURE:
<223> OTHER INFORMATION: Randomly generated sequence obtained from computer processing

<400> SEQUENCE: 13
tttgagtctg accgaaagtc agatgacccc ttgcctgcct tgtggcattt tccatagaag 60
agagtacaga aagagtatcc attcatggaa tatcgagga 99

<210> SEQ ID NO 14
<211> LENGTH: 100
<212> TYPE: DNA
<213> ORGANISM: Artificial Sequence
<220> FEATURE:
<223> OTHER INFORMATION: Randomly generated sequence obtained from computer processing

<400> SEQUENCE: 14
ttggtgtctg ctccaaagtc tgatgaccca tagcctttcc ttgtggcatt ttccatacga 60
gtaagtacag gacgaatatc catgcgtgga aaatcgaaga 100

<210> SEQ ID NO 15
<211> LENGTH: 100
<212> TYPE: DNA
<213> ORGANISM: Artificial Sequence
<220> FEATURE:
<223> OTHER INFORMATION: Randomly generated sequence obtained from computer processing

<400> SEQUENCE: 15
cttgagtccg ccacaaagtt ttatgaccca ttgcctatcc tggtggcatt atccatagaa 60
aaaagtacag taggagtatc cgttcatgga aaaacgacga 100

<210> SEQ ID NO 16
<211> LENGTH: 100
<212> TYPE: DNA
<213> ORGANISM: Artificial Sequence
<220> FEATURE:
<223> OTHER INFORMATION: Randomly generated sequence obtained from computer processing

<400> SEQUENCE: 16
cttgattctg ccccaaagtc tgatacccca atgcctttcc ttgtggcact atccatagaa 60
gaaagtgcag taggggtatc caggtaagga aaatcgagga 100

<210> SEQ ID NO 17
<211> LENGTH: 99
<212> TYPE: DNA
<213> ORGANISM: Artificial Sequence
<220> FEATURE:
<223> OTHER INFORMATION: Randomly generated sequence obtained from computer processing

<400> SEQUENCE: 17
tttgagtctg cctcaaagtc ttataaccca ttgccttttc ttgtggcatc ttccctagaa 60
aaggtccagt acgagtatcc attcatggat aaccgagga 99

<210> SEQ ID NO 18
<211> LENGTH: 100
<212> TYPE: DNA
<213> ORGANISM: Artificial Sequence
<220> FEATURE:
<223> OTHER INFORMATION: Randomly generated sequence obtained from computer processing

<400> SEQUENCE: 18
tttgagactg ccccaaagtc tgattatcca ttgtctgtcc ttggggcatt ttacatagaa 60
gaaagtacag taggagtata caatcctgga aaatcgagga 100

<210> SEQ ID NO 19
<211> LENGTH: 100
<212> TYPE: DNA
<213> ORGANISM: Artificial Sequence
<220> FEATURE:
<223> OTHER INFORMATION: Randomly generated sequence obtained from computer processing

<400> SEQUENCE: 19
tttgagtctg ccccacagac tgatgaccaa ttgcctttcg ttgtggtatt ttcgaaagaa 60
gaaagtacga taggagtatt cattcatggt taatcgagga 100

<210> SEQ ID NO 20
<211> LENGTH: 100
<212> TYPE: DNA
<213> ORGANISM: Artificial Sequence
<220> FEATURE:
<223> OTHER INFORMATION: Randomly generated sequence obtained from computer processing
<220> FEATURE:
<221> NAME/KEY: misc_feature
<222> LOCATION: (31)..(34)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (63)..(65)
<223> OTHER INFORMATION: n is a, c, g, or t
<220> FEATURE:
<221> NAME/KEY: misc_feature
<222> LOCATION: (70)..(73)
<223> OTHER INFORMATION: n is a, c, g, or t
<220> FEATURE:
<221> NAME/KEY: misc_feature
<222> LOCATION: (82)..(87)
<223> OTHER INFORMATION: n is a, c, g, or t

<400> SEQUENCE: 20
tttgagtctg ccccaaagtc tgatgaccca nnnnctttcc ttgtggccnt ttccatagaa 60
gannntacan nnngagtatc cnnnnnngga aaatcgagga 100

-continued

```
<210> SEQ ID NO 21
<211> LENGTH: 100
<212> TYPE: DNA
<213> ORGANISM: Artificial Sequence
<220> FEATURE:
<223> OTHER INFORMATION: Randomly generated sequence obtained from
      computer processing

<400> SEQUENCE: 21

tttgagtctg ccccaaagtc tgatgaccca ttggctttcc ttgtggcctt ttccatagaa     60

gaaaatacat tacgagtatc ctttcaggga aaatcgagga                          100
```